US007204980B2

(12) United States Patent
Clark

(10) Patent No.: US 7,204,980 B2
(45) Date of Patent: Apr. 17, 2007

(54) METHODS FOR INHIBITING VIRAL REPLICATION IN VIVO

(75) Inventor: Mike Clark, Lexington, KY (US)

(73) Assignee: Phoenix Pharmacologics, Inc., Lexington, KY (US)

(*) Notice: Subject to any disclaimer, the term of this patent is extended or adjusted under 35 U.S.C. 154(b) by 0 days.

(21) Appl. No.: 10/674,666

(22) Filed: Sep. 29, 2003

(65) Prior Publication Data
US 2004/0131604 A1 Jul. 8, 2004

Related U.S. Application Data

(60) Provisional application No. 60/427,497, filed on Nov. 18, 2002.

(51) Int. Cl.
A61K 38/43 (2006.01)
(52) U.S. Cl. ............... 424/94.1; 424/185.1; 424/190.1; 435/5; 435/180; 435/181; 435/188
(58) Field of Classification Search ............... 424/94.1, 424/94.4, 158.1, 161.1, 185.1, 190.1; 435/191, 435/188, 5, 180, 181
See application file for complete search history.

(56) References Cited

U.S. PATENT DOCUMENTS

| 4,179,337 A | 12/1979 | Davis et al. |
| 4,609,546 A | 9/1986 | Hiratani |
| 5,372,942 A | 12/1994 | McGarrity et al. |
| 5,447,722 A | 9/1995 | Lang et al. |
| 5,468,478 A | 11/1995 | Saifer et al. |
| 5,474,928 A | 12/1995 | Takaku et al. |
| 5,804,183 A | 9/1998 | Filpula et al. |
| 6,183,738 B1 | 2/2001 | Clark |
| 6,737,259 B1 | 5/2004 | Clark .................. 435/181 |

FOREIGN PATENT DOCUMENTS

| EP | 0 372 752 A2 | 6/1990 |
| JP | 2-053490 | 2/1990 |
| JP | 4-121187 | 4/1992 |
| WO | WO94/05332 | 3/1994 |
| WO | WO96/34015 | 10/1996 |
| WO | WO 99/42568 | 8/1999 |
| WO | WO 01/83774 A2 | 11/2001 |
| WO | WO 02/44360 A2 | 6/2002 |

OTHER PUBLICATIONS

Torre et al. Role of nitrix oxide in HIV-1 infection: friend or foe? Lancet Infect Dis. May 2002;(5): 273-80.*
Oberg et al. Screening for new agents. Eur. J. Clin. Microbol. Infect Dis., Jul. 1990, vol. 9, No. 7, p. 466-471.*
Saunders. Non-nucleoside inhibitors of HIV reverse transcriptase: screening sucesses-clinical failures. Drug Design and Discovery. 1992, vol. 8, pp. 255-263.*

Yarcoan et al. Correlations between the in vitro and in vivo activity of anti-HIV agents: implications for future drug development. J. Enzyme Inhibition. 1992, vol. 6, pp. 99-111.*
Wiltink et al. Antiviral drugs. Pharmaceutisch Weekblad Scientific edition. 1991, vol. 13, No. 2, pp. 58-69.*
Fields et al. Fields Virology. Lippincott Williams & Wilkins, 4th Edition, 2001, vol. 1,1137.*
Dev et al. Antiviral Therapy: Future Treatment of Hepatitis C: What's around the Corner. Infect. Med. 2001, vol. 21, No. 1: p. 28-36.*
Izzo et al. Pegylated arginine deiminase lowers hepatitis C viral titers and inhibits nitric oxide synthesis. Journal of Gastroenterology and Hepatology, published online Jul. 5, 2006.*
Sun, et al., "Incidence and cofactors of hepatitis C virus-related heptacellular carcinoma: a prospective study of 12,008 men in Taiwan," Am. J. Epidemiol. (2002) 157:674-682.
Herrine, "Approach to the patient with chronic haptitis C virus infection," Ann. Intern. Med. (2002) 136:747-757.
Hoofnagle, "Course and outcome of hepatitis C," Hepatology (2002) 36:S21-S29.
Lauer and Walker, " Hepatitis C virus infection," (2001) N.Engl. J. Med. (2001) 345:41-52.
Liang, et al., "Prognosis, natural history, treatment, and prevention of hepatitis C," Ann. Intern. Med. (2001) 132:296-305.
Shiratori, et al., "Interfereon therapy after tumor ablation improves prognosis in patients with hepatocellular carcinoma associated with hepatitis C virus," Ann. Intern. Med. (2003) 138:299-306.
Smith, et al., "Identification of novel tumor markers in hepatitis C virus-associated heptaocellular carcinoma," Cancer Res. (2003) 63:859-864.
Yoshizawa, "Hepatocellular carcinoma associated with hepatitis C virus infection in Japan. Projection to other countries foreseeable future," Oncology (2002) 62 (Supp. 1): 8-17.
Colombo, "Natural history and pathogenesis of hepatitis C virus related hepatocellular carcinoma," J. Hepatol. (1999) 31 (Supp 1):25-30.
El-Serag. "Hepatocellular carcinoma and hepatitis C in the United States." Hepatclogy (2002) 36:S74-S83.
Ryder, "Guidelines for the diagnosis and treatment of hepatocellular carcinoma (HCC) in adults," Gut (2003) 52 (Supp III): iii1-iii8.
El-Serag, "Global epidemiology of hepatocellular carcinoma," Clin. Liver Dis. (2001) 5:87-107.
DiMaio, et al., "Hepatocellular carcinoma: systemic treatments," J. Clin. Gastroenterol. (2002) 35 (Supp. 2):S109-S114.
Curley, et al., "Radiofrequency ablation of hepatocellular cancer in 110 patients with cirrhosis," Ann. Surg. (2000) 232:381-391.

(Continued)

Primary Examiner—Bruce R. Campell
Assistant Examiner—Emily M. Le
(74) Attorney, Agent, or Firm—Woodcock Washburn LLP

(57) ABSTRACT

The present invention is directed to methods of modulating viral replication in vivo comprising administering to an individual a therapeutically or prophylactically effective amount of a composition comprising arginine deiminase modified with polyethylene glycol, to methods of concurrently modulating viral replication and treating cancer, and to methods of modulating nitric oxide levels in a patient, among others.

41 Claims, No Drawings

OTHER PUBLICATIONS

Watkins and Curley, "Liver and bite ducts," in Clinical Oncology, 2nd ed., Abeloff, et al., eds., New York, pp. 1681-1748, 2000.
Ensor, et al., "Pegylated arginine deaminase (ADI-SS PEG 20,000 mw) inhibits human melanomas and hepatocellular carcinomas in vitro and in vivo," Cancer Res. (2002) 62:5443-5447.
Takaku, et al., "Chemical modification by polyethylene glycol of the antitumor enzyme arginine deaminase from Mycoplasma arginini," Jpn. J. Cancer Res. (1983) 84:1195-1200.
Takaku, et al., "In vivo anti-tumor activity of arginine deaminase purified from Mycoplasma arginini," Int. J. Cancer (1992) 51:244-249.
Sugimura. et al., "High sensitivity of human melanoma cell lines to the growth inhibiting activity of Mycoplasma arginini deaminase in vitro," Melanoma Res. (1992) 2:191-196.
Rose, "Amino acid requirements of man," Fed. Proc. (1949) 8:546-552.
Snyderman, et al., "The arginine requirement of the infant," J. Dis. Child (1959) 97:192.
Shen, et al., "Resistance to the anti-proliferative activity of recombinant arginie deaminase in cell culture correlates with the endogenous enzyme, argininosuccinate synthetase," Cancer Lett. (2003) 191:165-170.
Falck-Ytter, et al., "Surprisingly small effect of antiviral treatment in patients with hepatitis C," Ann Intern. Med. (2002) 136:288-292.
Fried, "Side effects of therapy of hepatitis C and their management," Hepatology (2002) 36:S237-S244.
Fried, et al., "PEGinterferon alpha-2a plus ribavirin for chronic hepatitis C infection," N. Engl. J. Med. (2002) 347:975-982.
Manns, et al., "PEGinterferon alpha-2b plus ribavirin compared with interferon alpha 2b plus ribavirin for initial treatment of chronic hepatitis c: a randomized trial." Lancel (2001) 358:958-965.
Dantzler and Lawitz, "Treatment of chronic hepatitis C in nonresponders to previous therapy," Curr. Gastroenterol. Rep. (2003) 5:78-85.
Masci, et al., "New and modified interferon alfas: preclinical and clinical data," Curr. Oncol. Rep. (2003) 5:108-113.
Chandler, et al., "Treatment of chronic hepatitis C: a systematic review," Hepatology (2002) 36:S135-S144.
DiBisceglie and Hoofnagle, "Optimal therapy of hepatitis C, " Hepatology (2002) 36:S121-S127.
Lindsay, "Introduction to therapy to hepatitis C." (2002) Hepatology (2002) 36:S114-S120.
Lopez-Guerrero and Carrasco, "Effect of nitric oxide on poliovirus infection of two human cell lines," J. Virol. (1998) 72:2538-2540.
Wedemeyer, et al., "Polyethylene glycol-interferon: current status in hepatitis C virus therapy," J. Gastroenterol. Hepatol. (2002) 17 (Supp 3):S344-S350.
McHutchinson, et al., "Interferon alfa-2b alone or in combination with ribavirin as intial treatment for chronic hepatitis C," N. Eng. J. Med. (1998) 339:1485-1492.
Diamond and Lee, "Use of antiviral therapy in patients with hepatitis C," Ann. Intern. Med. (2002) 137:1012.
Johnston and Hoth, "Present status and future prospects for HIV therapies," Science (1993) 260:1286-1293.
Richman, "HIV therapeutics," Science (1996) 272:1886-1888.
Christie and Chapman, "Combination therapy for chronic hepatitis C: interferon and ribavirin," Hosp. Med. (1999) 60:357.
Rouse, et al., "Dependence of adenovirus replication on arginina and inhibition of plaque formation by pleuropneumonia-like organisms," Virology (1963) 20:357-365.
Tankersley, "Amino acid requirements of herpes simplex virus in human cells, " J. Bacteriol. (1964) 87:608-613.
Goldblum, et al., "Effect of withdrawl of arginine and other amino acids on the synthesis of tumor and viral antigens of SV40 virus," J. Gen. Virol. (1968) 3:143-146.
Minishima and Benyesh-Melnick, "Arginine-dependent events in cytomegalovirus infection,"Bacteriol. Proc. (1969) 170:334-339.
Levine, et al., "Late stage synchronization of respiratory syncytial virus replication," Virology (1971) 45:390-400.
Winters, et al., "A non-functional arginine biosynthetic pathway in polyoma-infected mouse embryo cells," Biochem. Biophys. Res. Comm. (1972) 47: 1045-1051.
Iinuma, et al, "Studies on the assembly of Newcastle disease virus: an arginine-dependent step in virus replication," Virology (1973) 51:205-215.
Romano and Scarlata, "Amino acid requirements of measles virus HeLa cells," Arch. Gesamte Virus Forschung (1973) 43:359-366.
Lisok and Sominina, "Improved methods of influenza virus propagation I. Enhancement of virus reproduction in cell cultures," Arch. Virol. (1977) 21:234-240.
Holtermann, "Amino acid requirements for the propagation of vaccinia virus in Earle's L cells," J. Gen. Virol. (1969) 4:585-591.
Singer, et al., "Effect of mycoplasmas on vaccinia virus growth: requirement of arginine," Proc. Soc. Exp. Biol. Med. (1970) 133:1439-1442.
Obert, et al., "Arginine requirement for late mRNA transcription of vaccinia virus in KB cells," (1971) Biochem Biophys. Res. Comm. (1971) 44:362-367.
Archard and Williamson, "The effect of arginine deprivation on the replication of vaccinia virus," J. Gen. Virol. (1971) 12:249-258.
Cooke and Williamson, "Enhanced utilization of citrulline in rabbitpox virus-infected mouse sarcoma 180 cells," J. Gen. Virol. (1973) 21:339-348.
Abuchowski, et al., "Effect of covalent attachment of polyethylene glygol on immunogenicity and circulating life of bovine liver catalase," J. Biol. Chem. (1977) 252:3582-3586.
Abuchowski et al., "Treatment of L5178Y tumor-bearing BDF mice with a nonimmunogenic L-glutaminase-L-asparaginase," Cancer Treat, Rep. (1979) 63:1127-1132.
Gill et al., "Inhibition of cell division in L5178Y cells by arginine-degrading mycoplasmas: the role of arginie deaminase," Can. J. Microbiol. (1970) 16:415-419.
Hershfield, et al., "Treatment of adenosine deaminase deficiency with polyethylene glycol-modified adenosine deaminase," N. Eng. J. Med. (1987) 316:589-596.
Jaffe, et al., "Favorable remission induction rate with twice weekly doses of L-asparaginase," Cancer Res. (1973) 33:1-4.
Jones, "The effect of arginine deaminase on murine leukemic lymphoblasts," Ph.D. dissertation, Univ. Oklahoma, 1981, pp. 1-165.
Kamisaki, et al., "Reduction in immunogenicity and clearance rate of *Escherichia coli* L-asparaginase by modification with monomethoxypolyethylene glycol," J. Pharmacol. Exp. Ther. (1981) 216:410-414.
Kamisaki, et al., "Increased antitumor activity of *Escherichia coli* L-asparaginase by modification with monomethoxypolyethylene glycol." Gann. (1982) 73:470-474.
Kidd, "Asparaginase and cancer—yesterday and today," Cancer Res. (1970) 33:1-14.
Kondo, et al., "Cloning and sequence analysis of the arginine deaminase gene from Mycoplasma arginini," Mol. Gen. Genet. (1990) 221:81-86.
Misawa, et al., "High-level expression of Mycoplasma arginine deaminase in *Escherichia coli* and its efficient renaturation as an anti-tumor enzyme," J. Biotechnol. (1994) 36:145-155.
Miyazaki, et al., "Potent growth inhibition of human tumor cells in culture by arginine deaminase purified from a culture of a Mycoplasma-infected cell line," Cancer Res. (1990) 50:4522-4527.
Monfardini, et al. "A branched monomethoxypoly(ethylene glycol) for protein modification," Bioconj. Chem. (1995) 6:62-69.
Naoi, et al., "Alteration of the substrate specificity of Aspergilus oryzae beta-galactosidase by modification with polyethylene glycol," J. Appl. Biochem. (1984) 6:91-102.
Oginsky, "Isolation and determination of arginie and citruline," Meth. Enzymol. (1957) 3:639-642.
Ohno, et al., "Cloning and nucleotide sequence of th gene encoding arginine deaminase of Mycoplasma arginini," Infect. Immun. (1990) 58:3788-3795.
Park, et al., "Pharmacology of *Eschericia coli*-L-asparaginase polyethylene glycol adduct," Anticancer Res. (1981) 1:373-376.

Pyatak, et al., "Preparation of a polyethylene glycol: superoxide dismutase adduct, and an examination of its blood circulating life and anti-inflammatory activity," Res. Comm. Chem. Path. Pharmacol. (1980) 29:113-127.

Sayers, et al., "Rapid high-efficiency site-directed mutagenesis by the phosphorothioate approach," Biotechniques (1992) 13:592-596.

Stocks, et al., "A fluorimetric assay of the degree of modification of protein primary amines with polyethylene glycol," Anal. Biochem. (1986) 154:232-234.

Su, et al., "Cloning of cDNA for argininosuccinate synthetase mRNA and study of enzyme overproduction in a human cell line," J. Biol. Chem (1981) 256:11826-11831.

Sugimura, et al., "Identification and purification of arginine deaminase that originated from Mycoplasma arginini," Infect. Immun. (1990) 58:2510-2515.

Takaku, et al, "Anti-tumor activity of arginine deaminase from Mycoplasma arginini and its growth-inhibitory mechanism," Int. J. Cancer (1995) 86:840-846.

Teske, et al., "Polythylene glycol-L-asparaginase versus native L-asparaginase in canine non-Hodgkin's lymphoma," Eur. J. Cancer (1990) 26:891-895.

Zalipsky, et al., "Use of functionalized poly(ethylene glycol)s for modification of polypeptides," Polyethylene Glycol Chemistry: Biotechnical and Biomedical Applications, Harris, ed., Plenum, NY, 1992, pp. 347-370.

Dillon, et al., "Biochemical characterization of the arginine degrading enzymes arginase and arginine deaminase and their effect on nitric oxide production," Med. Sci, Monit. (2002) 8:CR248-CR253.

Thomas, et al., "Enzymic degradation of plasma arginine using arginine deaminase inhibits nitric oxide production and protects mice from the lethal effects of tumour necrosis factor aplha and endotoxin," Biochem. J. (2002) 363:581-587.

Izzo, F. et al., "Pegylated Arginine Deiminase Treatment of Patients with Unresectable Hepatocellular Carcinoma: Results from Phase I/II Studies", *Journal of Clinical Oncology*, 2004, 22(10), 1815-1822.

Curley, S.A. et al., "Regression of Hepatocellular Cancer in a Patients Treated with Arginine Deiminase", *Hepato-Gastroenterology*, 2003, 50, 1214-1216, XP 009071872.

Donnelly, K., "Hepatitis and Transfusions", *Nephrology Nursing Journal*, 2000, 27(5),538-539, XP 009071928.

Holtsberg, F.W. et al., "Poly(ethylene glycol) (PEG) Conjugated Arginine Deiminase: Effects of PEG Formulations on its Pharmacological Propoerties", *Journal of Controlled Release*, 2002, 80, 259-271.

* cited by examiner

METHODS FOR INHIBITING VIRAL REPLICATION IN VIVO

CROSS REFERENCE TO RELATED APPLICATIONS

The present application claims priority of application Ser. No. 60/427,497, filed Nov. 18, 2002, which is hereby incorporated by reference in its entirety.

FIELD OF THE INVENTION

The present invention is directed to methods for inhibiting viral replication, to methods for treating cancer, to methods for treating and/or inhibiting metastasis, and to methods for concurrently inhibiting viral replication and treating cancer or treating and/or inhibiting metastasis, and others.

BACKGROUND OF THE INVENTION

Viral infections are among the leading causes of death with millions of deaths each year being directly attributable to several viruses including hepatitis and HIV.

Hepatitis is a disease of the human liver. It is manifested with inflammation of the liver and is usually caused by viral infections. Several viruses such as hepatitis A, B, C, D, E and G are known to cause viral hepatitis. Among them, HBV and HCV are the most serious.

Hepatitis C virus (HCV) is pandemic with more than 170 million persons worldwide infected. Among viral diseases, it is 5 times more widespread that human immunodeficiency virus type 1 (HIV-1), and approximately 10,000 Americans will die this year from cirrhosis and hepatocellular carcinoma (HCC) resultant from chronic HCV infection (Sun C A, Wu D M, Lin C C, LU S N, You S L, Wang L Y, Wu M H, Chen C J. 2003. Incidence and cofactors of hepatitis C virus-related hepatocellular carcinoma: a prospective study of 12,008 men in Taiwan. Am J Epidemiol 157:674–682; Herrine S K. 2002. Approach to the patient with chronic hepatitis C virus infection. Ann Intern Med 136: 747–757; Hoofnagle J H. 2002. Course and outcome of hepatitis C. Hepatology 36:S21–S29; Lauer G M, Walker B D. 2001 Hepatitis C virus infection. N Engl J Med 345:41–52; Liang T J, Rehermann B, Seeff L B, Hoofnagle J H. 2001. Pathogenesis, natural history, treatment, and prevention of hepatitis C. Ann Intern Med 132:296–305). Furthermore, the prevalence of HCV continues to increase in the USA, Western Europe and Asia despite the institution of blood donor screening programs. Progression to chronic disease occurs in most HCV infected patients. In addition, HCV causes HCC in 1–4% annually of all chronically infected individuals. Moreover, HCC can occur even in those without cirrhosis (Shiratori Y, Shiina S, Teratani T, Imamura M, Obi S, Sato S, Koike Y, Yoshida H, Omata M. 2003. Interferon therapy after tumor ablation improves prognosis in patients with hepatocellular carcinoma associated with hepatitis C virus. Ann Int Med 138:299–306; Smith M W, Yue Z N, Geiss G K, Sadovnikova N Y, Carter V S, Boix L, Lazaro C A, Rosenberg G B, Bumgarner R E, Fausto N, Bruix J, Katze M G. 2003. Identification of novel tumor markers in hepatitis C virus-associated hepatocellular carcinoma. Cancer Res 63:859–864; Yoshizawa H. 2002. hepatocellular carcinoma associated with hepatitis C virus infection in Japan: projection to other countries in the foreseeable future. Oncology 62 (Suppl 1):8–17; Colombo M. 1999. Natural history and pathogenesis of hepatitis C virus related hepatocellular carcinoma. J Hepatology 31 (Suppl 1):25–30).

Given the current prevalence of HCV infection among persons 30 to 50 years of age, the incidence and mortality rates of HCC are estimated to double in the United States over the next 10 to 20 years (El-Serag HB. 2002. Hepatocellular carcinoma and hepatitis C in the United States. Hepatology 36:S74–S83). It is estimated that there are 500 million people infected with it worldwide. No effective immunization is currently available, and hepatitis C can only be controlled by other preventive measures such as improvement in hygiene and sanitary conditions and interrupting the route of transmission.

Today, there is no effective therapy for HCC except surgical resection (Ryder S D. 2003. Guidelines for the diagnosis and treatment of hepatocellular carcinoma (HCC) in adults. Gut 52 (Suppl III):iii1–iii8; El-Serag H B. 2002. Hepatocellular carcinoma and hepatitis C in the United States. Hepatology 36:S74–S83; El-Serag H B. 2001. Global epidemiology of hepatocellular carcinoma. Clin Liver Dis 5:87–107; DiMaio M, DeMaio E, Perrone F, Pegnata S, Daniele B. 2002. Hepatocellular carcinoma: systemic treatments. J Clin Gastroenterol 35 (Suppl. 2):S109–S114; Curley S A, Izzo F, Ellis L M, Vauthey J N, Vallone P. 2000. Radiofrequency ablation of hepatocellular cancer in 110 patients with cirrhosis. Ann Surg 232:381–391; Watkins K T, Curley Sa. 2000. Liver and bile ducts. In Clinical Oncology, $2^{nd}$ ed. Editors M D Abeloff, J O Armitage, A S Lichter, J E Niederhuber. New York: Churchill Livingstone, pp. 1681–1748). However, only <5% of HCC patients are surgical candidates and only ~1% actually undergo resection. Even among those resected, recurrence of HCC is common, especially in those infected with HCV.

Amino acid deprivation therapy is an effective means for the treatment of some cancers. Although normal cells do not require arginine, many cancer cell lines are auxotrophic for this amino acid. Thus, cancers, including but not limited to HCC, may be selectively killed by arginine deprivation therapy (Ensor C M, Holtsberg F W, Bomalaski J S, Clark M A. 2002. Pegylated arginine deiminase (ADI-SS PEG $_{20,000}$ mw) inhibits human melanomas and hepatocellular carcinomas in vitro and in vivo. Cancer Res 62:5443–5440; Takaku, H, Misawa, S, Hayashi H and Miyazaki K. (1993). Chemical modification by polyethylene glycol of the anti-tumor enzyme arginine deiminase from *Mycoplasma arginini*. Jpn. J. Cancer Res. 84:1195–1200; Takaku H, Takase M, Abe S, Hayashi H and Miyazaki K. (1992). In vivo anti-tumor activity of arginine deiminase purified from *Mycoplasma arginini*. Int. J. Cancer 51:244–249; Sugimura K, Ohno T, Kussyama T, Azuma I. 1992. High sensitivity of human melanoma cell lines to the growth inhibitory activity of *Mycoplasma arginini* deiminase in vitro. Melanoma Res. 2:191–196). High sensitivity of human melanoma cell lines to the growth inhibitory activity of *Mycoplasma arginini* deiminase in vitro. Melanoma Res. 2:191–196). This therapy is well tolerated as arginine is not an essential amino acid in humans (Rose W C. 1949. Amino acid requirements of man. Fed Proc 8:546–452, Snyderman, S., E., Boyer, A., and L. E. Holt 1959. The arginine requirement of the infant. J. Dis. Child. 97:192 and for review see Rodgers Q R. 1994. Species variation in arginine requirements. In *Proceedings from a Symposium Honoring Willard J. Visek—from Ammonia to Cancer and Gene Expression*. Special Publication 86—April 1994, Agriculture Experiment Station, University of Illinois, 211 Mumford Hall, Urbana, Ill. 61801, pp. 9–21, as it can be synthesized from citrulline. ADI converts extracellular arginine into citrulline which may be taken up by normal cells and converted into arginine intracellularly but not by cancer cells, especially HCC cells, because they lack the rate limiting enzyme argininosuccinate synthetase (Ensor C M, Holtsberg F W, Bomalaski J S, Clark M A. 2002. Pegylated arginine deiminase (ADI-SS PEG $_{20,000}$ mw) inhibits human melanomas and hepatocellular carcinomas in vitro and in vivo. Cancer Res 62:5443–5440). This inability to express argininosuccinate synthetase has recently been confirmed by others (Shen L J, Lin W C, Beloussow K, Shen W C. 2003. Resistance to the antiproliferative activity of recombinant arginine deiminase in cell culture correlates with the endogenous enzyme, argininosuccinate synthetase. Cancer Lett 191:165–170) We have extended this study of argininosuccinate synthetase deficiency to other tumors (Dillon B J, Prieto V G, Curley S A, Ensor C M, Holtsberg F W, Bomalaski J S, Clark M A. 2003. The method incidence and distribution of argininosuccinate synthetase deficiency in human cancers: a method for identifying cancers sensitive to arginine deprivation. Cancer (in press). Preliminary results from human clinical testing of ADI-SS PEG 20,000 mw indicates this therapy to be both safe and effective as an anti-cancer treatment.

Hepatitis B virus infection can lead to a wide spectrum of liver injury. Moreover, chronic hepatitis B infection has been linked to the subsequent development of hepatocellular carcinoma, a major cause of death. Current prevention of HBV infection is a hepatitis B vaccination which is safe and effective. However, vaccination is not effective in treating those already infected (i.e., carriers and patients).

Acquired immune deficiency syndrome (AIDS) is a fatal disease, reported cases of which have increased dramatically within the past several years. The AIDS virus was first identified in 1983. It has been known by several names and acronyms. It is the third known T-lymphotropic virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (LIV). Two distinct families of HIV have been described to date, namely HIV-1 and HIV-2. The acronym "HIV" is used herein to refer to human immunodeficiency viruses generically.

Herpes simplex virus (HSV) types 1 and 2 are persistent viruses that commonly infect humans; they cause a variety of troubling human diseases. HSV type 1 causes oral "fever blisters" (recurrent herpes labialis), and HSV type 2 causes genital herpes, which has become a major venereal disease in many parts of the world. No fully satisfactory treatment for genital herpes currently exists. In addition, although it is uncommon, HSV can also cause encephalitis, a life-threatening infection of the brain. (The Merck Manual, Holvey, Ed., 1972; Whitley, Herpes Simplex Viruses, In: Virology, 2nd Ed., Raven Press (1990)). A most serious HSV-caused disorder is dendritic keratitis, an eye infection that produces a branched lesion of the cornea, which can in turn lead to permanent scarring and loss of vision. Ocular infections with HSV are a major cause of blindness. HSV is also a virus which is difficult, if not impossible to cure.

Anti-Viral Therapies

There are several problems with current anti-viral therapies. First, there are relatively few effective antiviral drugs. Many of the existing anti-virals cause adverse or undesirable side-effects. Most effective therapies (such as vaccination) are highly specific for only a single strain of virus. Frequently the virus undergoes mutation such that it becomes resistant to either the drug or vaccine.

Many of the current treatments for viral infections revolve around interferon-α (IFN-α). It is believed that IFN-α binds to cellular receptors and initiates an intracellular response that includes enzymes involved in protein synthesis. This ultimately leads to the anti-viral activity/response. However, data from various clinical trials have shown that approximately 40% of patients treated with IFN-α initially responded to the therapy, but 70% of these relapsed after the treatment ended. (Damen, M., and Bresters, D., in H. W. (ed.): Curr. Stud. Hematol. Blood Transf., Darger Publishers 1998, Basel.) Overall, the long-term therapeutic effect and response was observed in only 10 to 30% of the patients. (Houghton, M., in Fields, B. N. et al., Fields Virology, Raven Publishers 1996, Philadelphia). In addition many side effects were observed such as severe flu, fatigue, muscle and head aches, even depression, weight loss and diarrhea. (Damen, M., and Bresters, D., in H. W. (ed.): Curr. Stud. Hematol. Blood Transf., Darger Publishers 1998, Basel.)

HCV therapy

The current standard therapy for HCV infection is pegylated (PEG) interferon-α (IFN) and ribavirin. Although this therapy can result in sustained anti-viral response, significant numbers of patients do not respond to this therapy or are excluded from this treatment (Falck-Ytter Y, Kale H, Mullen K D, Sarbah S A, Sorescu L, McCullough A J. 2002. Surprisingly small effect of antiviral treatment in patients with hepatitis C. Ann Intern Med 136:288–292; Fried M W. 2002. Side effects of therapy of hepatitis C and their management. Hepatology 36:S237–S244; Fried M W, Shiffinan M L, Reddy K R, Smith C, Marinos G, Gonçales F L Jr, Häussinger K, Diago M, Carosi G, Dhumeaux K, Craxi A, Lin A, Hoffman J, Yu J. 2002. Peginterferon alfa-2a plus ribavirin for chronic hepatitis C virus infection. N Engl J Med 347:975–982.; Herrine S K. 2002. Approach to the patient with chronic hepatitis C virus infection. Ann Intern Med 136:747–757; Lauer G M, Walker B D. 2001. Hepatitis C virus infection. N Engl J Med 345:41–52; Liang T J, Rehermann B, Seeff L B, Hoofnagle J H. 2001. Pathogenesis, natural history, treatment and prevention of hepatitis C. Ann Intern Med 132:296–305; Manns M P, McHutchinson J G, Gordon S C, Rustgi V K, Shiffman M, Reindollar R, Goodman Z D, Koury K, Ling M -H, Albrecht J K. 2001. Peginterferon alfa-2b plus ribavirin compared with interferon alfa-2b plus ribavirin for initial treatment of chronic hepatitis C: a randomized trial. Lancet 358:958–965). For example, recent studies of PEG-IFN α-2a (Pegasys$^{TN}$) plus ribavirin, and PEG-IFN α-2b (Pegintron$^{TN}$) plus ribavirin demonstrate that ~56% of studied patients had a sustained viral response (Dantzler T D, Lawitz E J. 2003. Treatment of chronic hepatitis C in nonresponders to previous therapy. Curr Gastroenterol Rep 5:78–85; Masci P, Bukowski R M, Patten P A, Osborn B L, Borden E C. 2003. New and modified interferon alfas: preclinical and clinical data. Curr Oncol Rep 5:108–113; Chandler G, Sulkowski M S, Jenckes M W, Torbenson M S, Herlong H F, Bass E B, Gebo K A. 2002. Treatment of chronic hepatitis C: a systematic review. Hepatology 36:S135–S144; DiBisceglie A M, Hoofnagle J H. 2002. Optimal therapy of hepatitis C. Hepatology 36:S121–127; Fried M W. 2002. Side effects of therapy of hepatitis C and their management. Hepatology 36:S237–S244; Lindsay K L. 2002. Introduction to therapy of hepatitis C. Hepatology 36:S114–S120. López-Guerrero J A, Carrasco L. 1998. Effect of nitric oxide on poliovirus infection of two human cell lines. J Virol 72:2538–2540; Wedemeyer H, Wiegand J, Cornberg M, Manns M P.; Polyethylene glycol-interferon: Current status in hepatitis C virus therapy, J Gastroenterol Hepatol. 2002 Dec; 17 Suppl 3:S344–S350; Manns M P, McHutchinson J G, Gordon S C, Rustgi V K, Shiffman M, Reindollar R, Goodman Z D, Koury K, Ling M -H, Albrecht J K. 2001. Peginterferon alfa-2b plus ribavirin compared with interferon alfa-2b plus ribavirin for initial treatment of chronic hepatitis C: a randomized trial. Lancet 358:958–965). However, for HCV genotypes 1a and 1b, the most common genotypes in the USA and western Europe, the response was only ~46%. HCV genotypes 2 and 3 had a better response (76%–82%). Furthermore, this response rate of ~50% is only for patients studied in clinical trials; it does not represent the entire patient population and is, therefore, biased ((Dantzler T D, Lawitz E J. 2003. Treatment of chronic hepatitis C in nonresponders to previous therapy. Curr Gastroenterol Rep 5:78–85; Masci P, Bukowski R M, Patten P A, Osborn B L, Borden E C. 2003. New and modified interferon alfas: preclinical and clinical data. Curr Oncol Rep 5:108–113; Chandler G, Sulkowski M S, Jenckes M W, Torbenson M S, Herlong H F, Bass E B, Gebo K A. 2002. Treatment of chronic hepatitis C: a systematic review. Hepatology 36:S135–S144; DiBisceglie A M, Hoofnagle J H. 2002. Optimal therapy of hepatitis C. Hepatology 36:S121–127; Fried M W. 2002. Side effects of therapy of hepatitis C and their management. Hepatology 36:S237–S244; Fried M W, Shiffman M L, Reddy K R, Smith C, Marinos G, Gonçales F L Jr, Häussinger K, Diago M, Carosi G, Dhumeaux K, Craxi A, Lin A, Hoffman J, Yu J. 2002. Peginterferon alfa-2a plus ribavirin for chronic hepatitis C virus infection. N Engl J Med 347:975–982; Lindsay K L. 2002. Introduction to therapy of hepatitis C. Hepatology 36:S114–S120. López-Guerrero J A, Carrasco L. 1998. Effect of nitric oxide on poliovirus infection of two human cell lines. J Virol 72:2538–2540; Wedemeyer 2002, Manns M P, McHutchinson J G, Gordon S C, Rustgi V K, Shiffman M, Reindollar R, Goodman Z D, Koury K, Ling M -H, Albrecht J K. 2001. Peginterferon alfa-2b plus ribavirin compared with interferon alfa-2b plus ribavirin for initial treatment of chronic hepatitis C: a randomized trial. Lancet 358:958–965). For example, a large study in the USA excluded 404 out of 1337 (or ~30%) of potential patients due to selection criteria (McHutchinson J G, Gordon S C, Schiff E R, Shiffinan M L, Lee W M, Rustgi V K, et al. 1998. Interferon alfa-2b alone or in combination with ribavirin as initial treatment for chronic hepatitis C. Hepatitis Interventional Therapy Group. N Engl J Med 339:1485–1492). Other large studies often fail to describe their screening criteria or the percentage of patients enrolled. A recent study performed in the USA by a large teaching hospital noted that 72% of all HCV patients were not treated with IFN for reasons such as medical or psychiatric contraindications, ongoing substance or alcohol abuse, failure to adhere to evaluation procedures, normal liver enzymes or even patient preference of no treatment (Falck-Ytter Y, Kale H, Mullen K D, Sarbah S A, Sorescu L, McCullough A J. 2002. Surprisingly small effect of antiviral treatment in patients with hepatitis C. Ann Intern Med 136:288–292). Similar results have been confirmed by others (Diamond C, Lee J H. 2002. Use of antiviral therapy in patients with hepatitis C. Annals Intern Med 137:1012). Thus a significant portion of the HCV infected population does not receive current "best standard of care" treatment due to a variety of medical or psychiatric contraindications. Even in studies using the "best" patients in the USA and western Europe, only ~50% achieve sustained viral response.

IFN-α also has significant side effects which occur with approximately the same frequency in both the PEG and non PEG formulated versions (Masci P, Bukowski R M, Patten P A, Osborn B L, Borden E C. 2003. New and modified interferon alfas: preclinical and clinical data. Curr Oncol Rep 5:108–113; Fried M W. 2002. Side effects of therapy of hepatitis C and their management. Hepatology 36:S237–S244; Wedemeyer 2002, Herrine S K. 2002. Approach to the patient with chronic hepatitis C virus infection. Ann Intern Med 136:747–757; Lauer G M, Walker B D. 2001. Hepatitis C virus infection. N Engl J Med 345:41–52; Liang T J, Rehermann B, Seeff L B, Hoofnagle J H. 2001. Pathogenesis, natural history, treatment, and prevention of hepatitis C. Ann Intern Med 132:296–305). These side effects include an influenza-like illness with fever, chills, myalgias and malaise in up to 82% of patients studied, with neuropsychiatric complications such as depression, irritability and depression and anxiety in ~20% of patients. Bone marrow suppression with granulocytopenia, anemia or thrombocytopenia occurs in ~5%, as does alopecia. These side effects are frequently so severe that further treatment with IFN alpha is discontinued, thus further limiting the utility of IFN therapy. Therefore, new treatments for HCV are needed.

HIV Therapy

Several drugs have been approved for treatment of HIV, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, Science, 260(5112), 1286–1293 (1993) and D. D. Richman, Science, 272(5270), 1886–1888 (1996). An alternative treatment for HCV has been ribavirin. Ribavirin is an anti-viral with a broad range of target viral activities. Ribavirin is a guanosine analogue harboring a modified base (1-β-D-ribo-furanosyl- -1,2,4-trizole-3-carboxamide), and has been proposed to inhibit the cellular enzyme inosine monophosphate dehydrogenase, resulting in a decrease of guanosine triphosphate. Damen, M., and Bresters, D., in H. W. (ed.): Curr. Stud. Hematol. Blood Transf., Darger Publishers 1998, Basel. However, ribavirin will cause side effects. Christie, J. M. and Chapman, R. W., Hosp Med. 60, 357 (1999). In particular ribavirin accumulates in the erythrocytes of patients and can cause hemolytic anemia.

An AIDS vaccine (Salk's vaccine) has been tested and several proteins which are chemokines from CD8 have been discovered to act as HIV suppressors. In addition to the above synthetic nucleoside analogs, proteins, and antibodies, several plants and substances derived from plants have been found to have in vitro anti-HIV activity. However, HIV virus is not easily destroyed nor is there a good mechanism for keeping the host cells from replicating the virus.

In vitro Use of Arginine Deprivation

Many studies over the last 30 years have demonstrated that extracellular arginine is required for viral replication in vitro. Historically this has been accomplished by making tissue culture media deficient in arginine and dialyzing the serum used as a supplement in order to achieve arginine free medium. Using this methodology to achieve arginine deprivation results in inhibition of replication of a large number of diverse families of viruses including: adeno virus (Rouse H C, Bonifas V H, Schlesinger R W. 1963. Dependence of adenovirus replication on arginine and inhibition of plaque formation by pleuropneumonia-like organisms. Virology 20:357–365), herpes virus (Tankersley R W Jr. 1964. Amino acid requirements of herpes simplex virus in human cells. J Bacteriol 87:608–613), SV 40 (Goldblum N, Ravid Z, Becker Y. 1968. Effect of withdrawal of arginine and other amino acids on the synthesis of tumour and viral antigens of SV40 virus. J Gen Virol 3:143–146), cytomegalovirus (Minamishima Y, Benyesh-Melnick M. 1969. Arginine-dependent events in cytomegalovirus infection. Bacteriol Proc 170:334–339), respiratory syncytial virus (Levine S, Buthala D, Hamilton R D. 1971. Late stage synchronization of respiratory syncytial virus replication. Virology 45:390–400), polyoma virus (Winters A L, Consigli R A, Rogers O R 1972. A non-functional arginine biosynthetic pathway in polyoma-infected mouse embryo cells. Biochem Biophys Res Comm 47:1045–1051), Newcastle disease virus (Ilnuma M, Maemo K, Matsumoto T. 1973. Studies on the assembly of Newcastle disease virus: an arginine-dependent step in virus replication. Virology 51:205–215), measles virus (Romano N, Scarlata G. 1973. Amino acid requirements of measles virus in HeLa cells. Arch Gesamte Virus Forschung 43:359–366), influenza (Lisok T P, Sominina A A. 1977. Improved methods of influenza virus propagation. I. Enhancement of virus reproduction in cell cultures. Acta Virol 21:234–240), and perhaps even more relevant, vaccinia virus (Holterman O A. 1969. Amino acid requirements for the propagation of vaccinia virus in Earle's L cells. J Gen Virol 4:585–591, Singer S H, Fitzgerald E A, Barile M F, Kirschstein R L. 1970. Effect of mycoplasmas on vaccinia virus growth: requirement of arginine. Proc Soc Exp Biol Med 133:1439–1442, Obert G, Tripier F, Guir J. 1971. Arginine requirement for late mRNA transcription of vaccinia virus in KB cells. Biochem Biophys Res Comm 44:362–367, Archard L C, Williamson J D. 1971. The effect of arginine deprivation on the replication of vaccinia virus. J Gen Virol 12:249–258.) and rabbit pox virus (Cooke B C, Williamson J D. 1973. Enhanced utilization of citrulline in rabbitpox virus-infected mouse sarcoma 180 cells. J Gen Virol 21:339–348). Vaccinia virus is the prototypical member of the Orthopoxvirus genera that includes smallpox (variola virus). Inhibition of viral replication is observed in vitro, even though protein synthesis and replication of infected cells is not affected.

Enzymes which degrade arginine are known and include arginine deiminase (ADI). However, a problem associated with the therapeutic use of such a heterologous protein is its antigenicity. The chemical modification of arginine deiminase from Mycoplasma arginini, via a cyanuric chloride linking group, with polyethylene glycol was described by Takaku, H, Misawa, S, Hayashi H and Miyazaki K. (1993). Chemical modification by polyethylene glycol of the anti-tumor enzyme arginine deiminase from *Mycoplasma arginini*. Jpn. J. Cancer Res. 84:1195–1200. However, the modified protein was toxic when metabolized due to the release of cyanide from the cyanuric chloride linking group.

There is a need for methods for inhibiting viral replication which do not have the problems associated with the prior art. The present invention is directed to these, as well as other, important ends.

SUMMARY OF THE INVENTION

The present invention is directed to methods of modulating viral replication comprising administering to a patient arginine deiminase bonded to polyethylene glycol. The present invention is also directed to methods of concurrently modulating viral replication and treating cancer, including, for example, sarcomas, hepatomas and melanomas. The present invention is also directed to methods of determining the susceptibility of an individual to arginine deprivation therapy for a viral infection, methods for improving liver function, and the like. These and other aspects of the present invention will be elucidated in the following detailed description of the invention.

DETAILED DESCRIPTION OF THE INVENTION

Overview

The present invention is based on the unexpected discovery that ADI modified with polyethylene glycol inhibits viral replication. ADI may be covalently bonded to polyethylene glycol with or without a linking group, although some embodiments utilize a linking group. PEG-20,000, for example, exhibits useful enzymatic activity levels, antigenicity, circulating half-life, efficacy, and relative ease of manufacture.

The mechanism by which lowering of extracellular arginine inhibits viral replication is not known. Herbivores such as human and mice (unlike carnivores which have an absolute requirement for arginine) (for review see Rodgers Q R. 1994. Species variation in arginine requirements. In *Proceedings from a Symposium Honoring Willard J. Visek—from Ammonia to Cancer and Gene Expression*. Special Publication 86—April 1994, Agriculture Experiment Station, University of Illinois, 211 Mumford Hall, Urbana, Ill. 61801, pp. 9–21) and most cells do not require arginine for growth as it may be synthesized from citrulline using two intracellular enzymes (argininosuccinate synthase and argininosuccinate lyase). Thus elimination of extracellular arginine dose not affect intracellular levels of arginine provided citrulline is available to the cells. As viral replication is an intracellular process, it is unexpected that a decrease in extracellular arginine could inhibit viral replication.

Although not wishing to be bound by theory, one possible mechanism by which lowering of extracellular arginine may inhibit viral replication is by inhibiting nitric oxide synthesis. Nitric oxide is synthesized from extracellular arginine, thus elimination of this arginine pool effectively inhibits the production of this important metabolite. Although nitric oxide is thought to be protective against some virus infections (Akaike T, Maeda H. 2000. Nitric oxide and virus infection. Immunology 101:300–308), inhibition of nitric oxide synthesis has been shown to block the replication of lymphocytic choriomeningitis virus (Campbell I L Samimi A, Chiang C S. 1994. Expression of the inducible nitric oxide synthase. Correlation with neuropathology and clinical features in mice with lymphocytic choriomeningitis. J Immunol 153:3622–3629) and HIV (Blond D, Raoul H, LeGrand R, Dormont D. 2000. Nitric oxide synthesis enhances human immunodeficiency virus replication in primary human macrophages. J Virol 74:8904–8912). Inhibition of nitric oxide synthesis has also been shown to protect animals from the lethal effects of influenza (Akaike T, Noguchi Y, Ijiri S, Setoguchi K, Suga M, Zheng Y M, Dietzschold B, Maeda H. 1996. Pathogenesis of influenza virus-induced pneumonia: involvement of both nitric oxide and oxygen radicals. Proc Natl Acad Sci USA 93:2448–2453; Karupiah G, Chen J -H, Mahalingam S, Nathan C F, MacMicking J D. 1998. Rapid interferon γ-dependent clearance of influenza A virus and protection from consolidating pneumonitis in nitric oxide synthase 2-deficient mice. J Exp Med 188:1541–1546), polio virus (López-Guerrero J A, Carrasco L. 1998. Effect of nitric oxide on poliovirus infection of two human cell lines. J Virol 72:2538–2540), rabies virus (Ubol S, Sukwattanapan C, Maneerat Y. 2001. Inducible nitric oxide synthase delays death of rabies virus-infected mice. J Med Microbiol 50:238–42) and flavivirus (Kreil T R, Eibl M M. 1996. Nitric oxide and viral infection: no antiviral activity against a flavivirus in vitro, and evidence for contribution to pathogenesis in experimental infection in vivo. Virology 219: 304–306). However, these previously used nitric oxide synthesis inhibitors have been limited by their toxicities (liver failure, seizure and death) in both animals and humans. Thus it is not clear that inhibition of viral replication resulting from elimination of arginine from the culture media (a process which clearly eliminates nitric oxide production) is the only mechanism by which inhibition of viral replication occurs. This stimulation/inhibition duality of nitric oxide and virus infection is also observed with nitric oxide in other pathological events (Colasanti M, Suzuki H. 2000. The dual personality of NO. Trends Pharm Sci 21:249–252). Thus inhibition of nitric oxide should not be expected to abrogate all sequella of an infectious event (Bogdan C. 2001. Nitric oxide and the immune system. Nature Immunology 2:907–916). However, unlike the nitric oxide synthesis inhibitors used in the past, ADI-PEG 20 appears to be safe and effective in inhibiting production of nitric oxide and can be used to help elucidate the role of this biomediator in protection against viral infection.

Definitions

Throughout the present disclosure, the following abbreviations may be used: PEG, polyethylene glycol; ADI, arginine deiminase; SS, succinimidyl succinate; SSA, succinimidyl succinamide; SPA, succinimidyl propionate; and NHS, N-hydroxy-succinimide.

ADI covalently modified with polyethylene glycol (with or without a linking group) may be hereinafter referred to as "ADI-PEG", or "PEG-ADI".

"Polyethylene glycol" or "PEG" refers to mixtures of condensation polymers of ethylene oxide and water, in a branched or straight chain, represented by the general formula $H(OCH2CH2)_nOH$, wherein n is at least 4. "Polyethylene glycol" or "PEG" is used in combination with a numeric suffix to indicate the approximate weight average molecular weight thereof. For example, PEG-5,000 (PEG5) refers to polyethylene glycol molecules having an average molecular weight of about 5,000; PEG-12,000 (PEG12) refers to polyethylene glycol molecules having an average molecular weight of about 12,000; and PEG-20,000 (PEG20) refers to polyethylene glycol molecules having an average molecular weight of about 20,000.

As used herein, the term "individual" refers to an animal, in some embodiments a mammal, and in some embodiments a human. The term "individual" includes biological samples taken from such animals.

As used herein, the term "viral disease" refers to diseases and disorders caused by a virus. Viral diseases include without limitation viruses that infect animals or mammals, including humans. Human viruses include viruses from the following viral families: Pox, Herpes, Adeno, Papova, Parvo, Hepadna, Picorna, Calici, Astro, Toga, Flavi, Corona, Paramyxo, Orthomyxo, Bunya, Arena, Rhabdo, Filo, Borna, Reo, and Retro.

Examples of viruses and associated diseases that may be treated by the present invention include without limitation: variola (smallpox); herpesviruses, such as herpes simplex virus (cold sores), varicella-zoster (chicken pox, shingles), Epstein-Barr virus (mononucleosis, Burkitt's lymphoma), KSHV (Kaposi's sarcoma), and cytomegalovirus (blindness); adenoviruses; hepatitis (A/B/C); polioviruses, rhinociruses, rubella, yellow fever, West Nile virus, dengue, equine encephalitis, respiratory syncytial virus (RSV), parainfluenza virus, and tobacco mosaic virus.

In some embodiments the virus is one or more of HIV, influenza, polio viruses, herpes simplex, hepatitis B, hepatitis C and other viral strains of hepatitis, Kaposi's sarcoma, rhinoviruses, West Nile virus, smallpox, and vaccinia, among others.

As used herein, "modulation" means either an increase (stimulation) or a decrease (inhibition) in the expression of a gene. In some embodiments of the present invention, inhibition is the form of modulation of gene expression.

As used herein, the term "inhibit" refers to a reduction or decrease in a quality or quantity, compared to a baseline. For example, in the context of the present invention, inhibition of viral replication refers to a decrease in viral replication as compared to baseline. In some embodiments there is a reduction of about 30%, about 40%, about 50%, about 60%, about 70%, about 75%, about 80%, about 85%, about 90%, about 95%, about 99%, and about 100%. Those of ordinary skill in the art can readily determine whether or not viral replication has been inhibited and to what extent.

As used herein, the term "about" refers to +/–20%, +/–15%, +/–10%, or +/–5% of the value.

As used herein, the term "biocompatible" refers to materials or compounds which are generally not injurious to biological functions and which will not result in any degree of unacceptable toxicity, including allergenic and disease states.

"Circulating half life" refers to the period of time, after injection of the modified ADI into a patient, until a quantity of the ADI has been cleared to levels one half of the original peak serum level. Circulating half-life may be determined in any relevant species, including humans or mice.

As used herein, the terms "covalently bonded", "bonded" and "coupled" are used interchangeably and refer to a covalent bond linking ADI to the PEG molecule, either directly or through a linker.

As used herein, the term "therapeutically effective amount" is meant an amount of a compound of the present invention effective to yield the desired therapeutic response. The specific therapeutically effective amount will, obviously, vary with such factors as the particular condition being treated, the physical condition of the patient, the type of mammal or animal being treated, the duration of the treatment, the nature of concurrent therapy (if any), and the specific formulations employed and the structure of the compounds or its derivatives. In the context of improving liver function, the term "therapeutically effective amount" refers to an amount of arginine deiminase bonded to polyethylene glycol that improves liver function. In some embodiments the therapeutically effective amount is effective to improve the Child-Pugh scale or the Mayo End-stage Liver Disease (MELD) score of the individual. In some embodiments the therapeutically effective amount is effective to improve liver function based on comparison of markers of liver function including, without limitation, billrubin levels, creatine levels, and international normalized ratio.

As used herein, the term "an amount effective to inhibit viral replication" refers to the amount of a compound comprising ADI covalently bonded via a linking group to polyethylene glycol administered to an individual that results in a reduced level of viral replication and thus a reduced amount of detectable virus in the individual, i.e., a reduction in viral titer or viral load. To determine an amount effective to inhibit viral replication, the individual's viral load can be determined prior to treatment with a compound of the present invention and then subsequent to treatment. The level of viral replication can be quantified by any number of routine methodologies including, for example: quantifying the actual number of viral particles in a sample prior to and subsequent to compound administration, and quantifying the level of one or more viral antigen present in a sample prior to and subsequent to compound administration. In some embodiments "an amount effective to inhibit viral replication" is the amount necessary to decrease plasma arginine concentrations below about 5 µM. Methods of measuring plasma arginine concentrations are well known in the art.

Assays for viral replication also provide one with the ability to determine the efficacy of viral inhibitors and are well known to those skilled in the art. Such assays may be conducted in vivo or in vitro. HCV is known to occur in chimpanzees where the infection closely resembles that seen in humans. There have also been reports of experimental infection in tupaias, closely related to the primates, and in immunodeficient mice. (Xie, Z. C. et al., Virology, 244, 513 (1998); Schinazi, R. F. et al., Antiviral Chem. Chemother. 10, 99, (1999)).

The inhibition of viral replication contributes to a reduction in the severity of the viral infection or of the symptoms of the viral infection.

As used herein, the term "prophylactically effective amount" is meant an amount of a compound of the present invention effective to yield the desired prophylactic response. The specific prophylactically effective amount will, obviously, vary with such factors as the particular virus, the physical condition of the patient, the type of mammal or animal being treated, the duration of the treatment, the nature of concurrent therapy (if any), and the specific formulations employed and the structure of the compounds or its derivatives As used herein "combination therapy" means that the individual in need of treatment is given another drug for the disease in conjunction with PEG-ADI. This combination therapy can be sequential therapy where the individual is treated first with one or more drugs and then the other, or two or more drugs are given simultaneously.

As used herein, the phrase "arginine deprivation therapy" refers to a treatment regimen that involves the use of an agent that reduces, minimizes, or abolishes arginine levels in the patient. Arginine deprivation therapy is often performed using ADI. Arginine deprivation therapy and agents used in arginine deprivation therapy are described in detail in allowed U.S. application Ser. No. 09/023,809, filed Feb. 13, 1998, now U.S. Pat. No. 6,183,738, issued Feb. 6, 2001; and pending application U.S. Ser. No. 09/504, 280, filed Feb. 15, 2000, each of which is hereby incorporated by reference in its entirety.

As used herein, the term "an individual suspected of having been exposed to one or more viruses" refers to an individual who has not been diagnosed as being positive for one or more viruses but who could possibly have been exposed to one or more viruses due to a recent high risk activity or activity that likely put them in contact with the viruses. For example, an individual suspected of having been exposed to HIV refers to an individual that has been stuck with a needle that has been in contact with either a sample that contains HIV or HIV infected individual. Examples of such samples include, without limitation, laboratory or research samples or samples of blood, semen, bodily secretions, and the like from patients. Individuals suspected of being exposed to HCV include individuals that have received blood transfusions with blood of unknown quality. The blood that is being transfused may have not been tested or the test results indicating that the blood does not contain HCV are not reliable or are doubted. In some embodiments, an individual suspected of being infected with a virus includes individuals who have been exposed to the virus through another individual including, for example, through sexual intercourse, contact with bodily fluids of another individual, sharing of hypodermic needles, and the like. The individual from which the virus originated may or may not have been tested for the presence and/or absence of the virus. The term "an individual suspected of having been exposed to one or more viruses" also includes individuals who have been diagnosed as being positive for one virus but are also infected with at least one further virus. For example, often those infected with HIV are also positive for one or more forms of hepatitis. Such an individual may be classified as being at "high-risk" for one or more viruses.

As used herein, the term "selectively inhibit" refers selective inhibition of viral replication and is, in some embodiments, the ratio of $CC_{50}/IC_{50}$% of viral mRNA levels. An SI>10 is considered to reflect a selective inhibition of viral replication.

As used herein, the term "sample" refers to biological material from a patient. The sample assayed by the present invention is not limited to any particular type. Samples include, as non-limiting examples, single cells, multiple cells, tissues, tumors, biological fluids, biological molecules, or supernatants or extracts of any of the foregoing. Examples include tissue removed for biopsy, tissue removed during resection, blood, urine, lymph tissue, lymph fluid, cerebrospinal fluid, mucous, and stool samples. The sample used will vary based on the assay format, the detection method and the nature of the tumors, tissues, cells or extracts to be assayed. Methods for preparing samples are well known in the art and can be readily adapted in order to obtain a sample that is compatible with the method utilized.

ADI

Arginine deiminase catalyzes the conversion of arginine to citrulline, and may be used to eliminate arginine. In the present invention, the arginine deiminase gene may be derived, cloned or produced from any source, including, for example, microorganisms, recombinant biotechnology or any combination thereof. Arginine deiminase may be cloned from microorganisms of the genus *Mycoplasma*. In some embodiments, the arginine deiminase is cloned from *Mycoplasma arginini, Mycoplasma hominis, Mycoplasma arthritidis*, or any combination thereof. In some embodiments, the arginine deiminase used in the present invention may have one or more of the amino acid sequences of SEQ ID NOS: 1–10 and 13–21.

Native arginine deiminase may be found in microorganisms and is antigenic and rapidly cleared from circulation in a patient. These problems may be overcome by covalently modifying arginine deiminase with polyethylene glycol (PEG). Arginine deiminase covalently modified with polyethylene glycol (with or without a linking group) may be hereinafter referred to as "ADI-PEG." When compared to native arginine deiminase, ADI-PEG retains most of its enzymatic activity, is far less antigenic, has a greatly extended circulating half-life, and is much more efficacious in the treatment of tumors.

Certain disadvantages have come to be associated with the isolation of arginine deiminase from organisms. Although effective in killing tumor cells in vitro, arginine deiminase isolated from *Pseudomonas pudita* failed to exhibit efficacy in vivo because it had little enzyme activity at a neutral pH and was rapidly cleared from the circulation of experimental animals. Arginine deiminase derived from *Mycoplasma arginini* (SEQ ID NO:5) is described, for example, by Takaku H, Takase M, Abe S, Hayashi H and Miyazaki K. (1992). In vivo anti-tumor activity of arginine deiminase purified from *Mycoplasma arginini*. Int. J. Cancer 51:244–249, and U.S. Pat. No. 5,474,928, the disclosures of which are hereby incorporated by reference herein in their entirety. A problem associated with the therapeutic use of such a heterologous protein is its antigenicity. The chemical modification of arginine deiminase from *Mycoplasma arginini*, via a cyanuric chloride linking group, with polyethylene glycol was described by Takaku, H, Misawa, S, Hayashi H and Miyazaki K. (1993). Chemical modification by polyethylene glycol of the anti-tumor enzyme arginine deiminase from *Mycoplasma arginini*. Jpn. J. Cancer Res. 84:1195–1200. The modified protein was toxic when metabolized due to the release of cyanide from the cyanuric chloride linking group.

The production of arginine deiminase via recombinant DNA techniques also provides for certain disadvantages. For example, arginine deiminase produced in *Escherichia coli* is enzymatically inactive and thus must be denatured and then properly renatured in order for it to become enzymatically active. The usual method for renaturing arginine deiminase produced in *E. coli* is to isolate the inactive enzyme, dissolve it in guanidinium hydrochloride and renature it by rapid dilution into low ionic strength buffer. This last step requires very large volumes of buffer thus making the manufacture of arginine deiminase both expensive and time consuming. However, recombinant technology does have certain advantages. For example, organisms more amenable to fermentation can be used as hosts. Additionally, these fermentation hosts are generally much less pathogenic and larger amounts of arginine deiminase can be obtained. It has been shown the *E. coli* may produce large amounts of *Mycoplasma arginine* deiminase.

Chemical and genetic modification of the arginine deiminase enzyme can affect its biological activities. For example, it has been shown that arginine deiminase is typically antigenic and rapidly cleared from circulation in a patient. However, it has also been shown that the formulation of arginine deiminase with polyethylene glycol reduces the antigenicity and increases the circulating half-life of the enzyme. Abuchowski et al., Cancer Biochem. Biophys. 7:175–186 (1984); Abuchowski et al., J. Biol. Chem. 252: 3582–3586 (1977). In particular, arginine deiminase can be covalently modified with polyethylene glycol. Arginine deiminase covalently modified with polyethylene glycol (with or without a linking group) may be hereinafter referred to as "ADI-PEG." In U.S. patent application Ser. No. 09/023,809, Clark describes improved modifications of arginine deiminase from *Mycoplasma hominis* (SEQ ID NO:1), *Mycoplasma arginini* (SEQ ID NO:5), and *Mycoplasma arthritidis* (SEQ ID NO:7) with polyethylene glycol, the disclosure of which is hereby incorporated by reference herein in its entirety. When compared to native arginine deiminase, ADI-PEG retains most of its enzymatic activity, is far less antigenic, has a greatly extended circulating half-life, and is much more efficacious in the treatment of tumors. For purposes of the invention, the modification of any arginine deiminase with polyethylene glycol may be referred to as pegylation.

It is to be understood that arginine deiminase derived from other organisms may also have pegylation sites corresponding to 112 position of arginine deiminase from *Mycoplasma hominis*. For example, arginine deiminase from *Streptococcus pyogenes* has lysine at the 104 position, arginine deiminase from *Mycoplasma pneumoniae* has lysine at the 106 position, and arginine deiminase from *Giardia intestinalis* has lysine at the 114 position. In addition, arginine deiminase from some organisms may have lysines corresponding to the same general location as the 112 position of arginine deiminase from *Mycoplasma hominus*. The location of lysine in arginine deiminase from such organisms may be indicated as follows:

TABLE 1

Pegylation sites of arginine deiminase from various organisms

| Organisms producing arginine deiminase | Position of lysine in arginine deiminase |
| --- | --- |
| *Mycoplasma hominis* (SEQ ID NO: 1) | 112 |
| *Mycoplasma arginini* (SEQ ID NO: 5) | 111 |
| *Clostridium perfringens* (SEQ ID NO: 18) | 105 |
| *Bacillus licheniformis* (SEQ ID NO: 19) | 97, 108 |
| *Borrelia burgdorferi* (SEQ ID NO: 15) | 102, 111 |
| *Borrelia afzelii* (SEQ ID NO: 16) | 101 |
| *Enterococcus faecalis* (SEQ ID NO: 20) | 102, 110 |
| *Streptococcus pyogenes* (SEQ ID NO: 13) | 104 |
| *Streptococcus pneumoniae* (SEQ ID NO: 14) | 103 |
| *Lactobacillus sakei* (SEQ ID NO: 21) | 97, 106 |
| *Giardia intestinalis* (SEQ ID NO: 17) | 114, 116 |

It is presently believed that the attachment of polyethylene glycol to such lysines or combinations thereof may inactivate the enzyme. It is presently believed that amino acid substitutions at such lysines may result in a protein that loses less of its enzymatic activity upon pegylation.

In some embodiments the present invention provides for certain amino acid substitutions in the polypeptide chain of arginine deiminase. These amino acid substitutions provide for modified arginine deiminase that loses less activity upon pegylation; i.e. upon pegylation, the reduction of enzyme activity following pegylation in the modified arginine deiminases is less than the reduction of enzyme activity following pegylation in the unmodified arginine deiminases. By eliminating pegylation sites at or adjacent to the catalytic region of enzyme, optimal pegylation can be achieved without the traditional loss of activity. As discussed above, arginine deiminase from certain organisms have pegylation sites located at various positions on the peptide chain. While not limiting the present invention, it is presently believed that arginine deiminase may have the amino acid lysine located at or adjacent to the catalytic region of the enzyme and that pegylation of these sites may inactivate the enzyme. By eliminating at least one of these pegylation sites, pegylation can be achieved and more enzyme activity retained. In accordance with the invention, in some embodiments lysine is substituted with glutamic acid, valine, aspartic acid, alanine, isoleucine, leucine or combinations thereof. In some embodiments lysine is substituted with glutamic acid. In some embodiments of the invention, modified arginine deiminase from *Mycoplasma hominis* has an amino acid substitution at $Lys^{112}$, $Lys^{374}$, $Lys^{405}$, $Lys^{408}$ or combinations or subcombinations thereof. In some embodiments modified arginine deiminase from *Mycoplasma hominis* has an amino acid substitution $Lys^{112}$ to $Glu^{112}$, $Lys^{374}$ to $Glu^{374}$, $Lys^{405}$ to $Glu^{405}$, $Lys^{408}$ to $Glu^{408}$ or combinations thereof. In some embodiments modified arginine deiminase from *Mycoplasma hominis* has lysine at position 112 substituted with glutamic acid (SEQ ID NO:2).

The present invention thus provides for certain amino acid substitutions in the polypeptide chain of arginine deiminase. Such amino acid substitutions can eliminate the problematic structural characteristics in the peptide chain of arginine deiminase. Such amino acid substitutions provide for improved renaturation of the modified arginine deiminase. These amino acid substitutions make possible rapid renaturing of modified arginine deiminase using reduced amounts of buffer. These amino acid substitutions may also provide for increased yields of renatured modified arginine deiminase. In some embodiments of the invention, the modified arginine deiminase has a single amino acid substitution at Pro$^{210}$. As mentioned above, arginine deiminase derived from *Mycoplasma hominis* has the amino acid proline located at the 210 position. While not limiting the present invention, it is presently believed that the presence of the amino acid proline at position 210 results in a bend or kink in the normal polypeptide chain that increases the difficulty of renaturing (i.e., refolding) arginine deiminase. Substitutions for proline at position 210 may make possible the rapid renaturation of modified arginine deiminase using reduced amounts of buffer. Substitutions for proline at position 210 may also provide for increased yields of renatured modified arginine deiminase. In some embodiments, the proline at position 210 is substituted with serine (SEQ ID NO:3). It is to be understood that in accordance with this aspect of the invention, other substitutions at position 210 may be made. Examples of substitutions include Pro$^{210}$ to Thr$^{210}$, Pro$^{210}$ to Arg$^{210}$, Pro$^{210}$ to Asn$^{210}$, Pro$^{210}$ to Gln$^{210}$ or Pro$^{210}$ to Met$^{210}$. By eliminating those structural characteristics associated with the amino acid of position 210 of the wild-type arginine deiminase, proper refolding of the enzyme can be achieved.

In some embodiments of the invention, the modified arginine deiminase has multiple amino acid substitutions. The modified arginine deiminase may have at least one amino acid substitution eliminating pegylation sites at or adjacent a catalytic region of the enzyme. The modified arginine deiminase may also have at least one amino acid substitution eliminating those structural characteristics that interfere with the renaturation of the enzyme. The amino acid substitutions may thus provide for a modified arginine deiminase of the invention. The amino acid substitutions may provide for the pegylation of modified arginine deiminase without a loss of enzymatic activity. The amino acid substitutions may provide for a modified arginine deiminase that can be rapidly renatured using reduced amounts of buffer. The amino acid substitutions may also provide for increased yields of renatured modified arginine deiminase. In some embodiments, the modified arginine deiminase derived from *Mycoplasma hominis* includes the proline at position 210 substituted with serine and the lysine at position 112 substituted with glutamic acid (SEQ ID NO:4). As discussed above, however, it is to be understood that the modified arginine deiminase may include other substitutions. In some embodiments, conservative substitutions may be made at positions 112 and/or 210 of the wild-type arginine deiminase.

Modified arginine deiminase was expressed in JM101 cells as previously described by Takaku et al., supra. The modified arginine deiminase included glutamic acid at the 112 position and serine at the 210 position. In some embodiments the amino acid sequence of modified arginine deiminase from *Mycoplasma hominis* is a sequence of SEQ ID NO:4.

In some embodiments arginine deiminase is derived from *Mycoplasma hominis, Mycoplasma pneumoniae, Mycoplasma arginini, Giardia intestinalis, Clostridium perfringens, Bacillus licheniformis, Borrelia burgdorferi, Borrelia afzelii, Enterococcus faecalis, Streptococcus pyogenes, Streptococcus pneumoniae, Lactobacillus sakei* or *Giardia intestinalis* arginine deiminase.

In some embodiments arginine deiminase is derived from *Mycoplasma hominis* arginine deiminase (SEQ ID NO:1). In some embodiments, the arginine deiminase comprises at the substitution or deletion of at least one proline residue as compared to SEQ ID NO:1. In some embodiments, the substitution or deletion of at least one proline residue comprises substitution or deletion of the proline residue at or corresponding to residue 210 of SEQ ID NO:1. In some embodiments, the substitution or deletion of at least one proline residue comprises substitution of the proline residue at or corresponding to residue 210 of SEQ ID NO:1 with Ser, Thr, Arg, Asn, Gln, or Met. In some embodiments, the substitution or deletion of at least one proline residue comprises substitution of the proline residue at or corresponding to residue 210 of SEQ ID NO:1 with Ser.

In some embodiments of the present invention the arginine deiminase is modified and comprises at least one amino acid substitution or deletion wherein the modified arginine deiminase has a reduced number of pegylation sites at or adjacent to a catalytic region, as compared to SEQ ID NO:1. In some embodiments, the substitution or deletion of at least one lysine residue comprises the substitution or deletion of at least one lysine residue at or corresponding to residues 112, 374, 405 or 408 of SEQ ID NO:1. In some embodiments, the substitution or deletion of at least one lysine residue comprises the substitution of at least one lysine residue at or corresponding to residues 112, 374, 405 or 408 of SEQ ID NO:1 with Glu, Val, Asp, Ala, Ile or Leu. In some embodiments, the substitution or deletion of at least one lysine residue comprises substitution of the lysine residue at or corresponding to residue 112 of SEQ ID NO:1 with Glu, Val, Asp, Ala, Ile or Leu. In some embodiments, the substitution or deletion of at least one lysine residue comprises substitution of the lysine residue at or corresponding to residue 112 of SEQ ID NO:1 with Glu. In some embodiments, the modified arginine deiminase comprises the further substitution or deletion of at least one proline residue.

In some embodiments, the substitution or deletion of at least one proline residue comprises substitution of the proline residue at or corresponding to residue 210 of SEQ ID NO:1 with Ser, Thr, Arg, Asn, Gln, or Met.

In some embodiments the arginine deiminase comprises arginine deiminase modified to be free of at least one pegylation site at or adjacent to a catalytic region as compared to SEQ ID NO:1, wherein said modified arginine deiminase comprises at least one amino acid substitution or deletion at or corresponding to residues 112, 374, 405, or 408 of SEQ ID NO:1. In some embodiments the at least one amino acid substitution or deletion comprises substitution of the lysine residue at or corresponding to residue 112 of SEQ ID NO:1 with Glu, Val, Asp, Ala, Ile or Leu. In some embodiments the at least one amino acid substitution or deletion further comprises substitution or deletion of at least one proline residue. In some embodiments the substitution or deletion of at least one proline residue comprises substitution or deletion of the proline residue at or corresponding to residue 210 of SEQ ID NO:1. In some embodiments the substitution or deletion of at least one proline residue comprises substitution of the proline residue at or corresponding to residue 210 of SEQ ID NO:1 with Ser, Thr, Arg, Asn, Gln, or Met.

In some embodiments the arginine deiminase from *Mycoplasma hominis* comprises a substitution of lysine at residue 112 of SEQ ID NO:1 with glutamic acid (SEQ ID NO:2). In some embodiments the arginine deiminase from *Myco-

*plasma hominis* comprises a substitution of proline at residue 210 of SEQ ID NO:1 with serine (SEQ ID NO:3). In some embodiments the arginine deiminase from *Mycoplasma hominis* comprises a substitution of lysine at residue 112 of SEQ ID NO:1 with glutamic acid and a substitution of proline at residue 210 of SEQ ID NO:1 with serine (SEQ ID NO:4). In some embodiments arginine deiminase from *Mycoplasma arginini* comprises a substitution of lysine at residue 111 of SEQ ID NO:5 with glutamic acid (SEQ ID NO:6). In some embodiments the arginine deiminase from *Mycoplasma arthritidis* comprises substitutions of lysine at residues 111 and 112 of SEQ ID NO:7 with glutamic acid (SEQ ID NO:8). In some embodiments the arginine deiminase from *Mycoplasma arthritidis* comprises a substitution of lysine at residue 111 of SEQ ID NO:7 with glutamic acid (SEQ ID NO:9). In some embodiments the arginine deiminase from *Mycoplasma arthritidis* comprises a substitution of lysine at residue 112 of SEQ ID NO:7 with glutamic acid (SEQ ID NO:10).

Such modifications and/or substitutions as well as nucleotide and polypeptide sequences are described in U.S. Pat. No. 6,183,738, issued Feb. 6, 2001, and co-pending application Ser. No. 09/564,559, filed May 4, 2000, each of which is hereby incorporated by reference in its entirety.

Polyethylene Glycol

There are many polyethylene glycols available that differ in their molecular weight and linking group. These PEGs can have varying effects on the antigencity, immunogenicity and circulating half-life of a protein (Zalipsky, S. and Lee, C. Polyethylene Glycol Chemistry: Biotechnical and Biomedical Applications. Pp. 347–370, Plenum Press, New York, 1992; Monfardini, C., et. al. bioconjugate Chem. 6, 62–69, 1995; Delgado C; Francis G E; Fisher D. The uses and properties of PEG-linked proteins. Crit. Rev. Ther. Drug Carrier Sys., 9:249–304, 1992.)

In some embodiments of the present invention, each polyethylene glycol molecule has an average molecular weight of about 10,000 to about 50,000; from about 12,000 to about 40,000, from about 15,000 to about 30,000; and about 20,000. Generally, polyethylene glycol with a molecular weight of 30,000 or more is difficult to dissolve, and yields of the formulated product are greatly reduced.

The polyethylene glycol may be a branched or straight chain. In some embodiments the polyethylene glycol is a straight chain. Increasing the molecular weight of the polyethylene glycol generally tends to decrease the immunogenicity of the ADI. The polyethylene glycols having the molecular weights described in the present invention may be used in conjunction with ADI, and, optionally, a biocompatible linking group, to treat viral diseases.

Pegylation

ADI may be covalently bonded to PEG via a biocompatible linking group, using methods known in the art, as described, for example, by Park et al, Anticancer Res., 1:373–376 (1981); and Zaplipsky and Lee, Polyethylene Glycol Chemistry: Biotechnical and Biomedical Applications, J. M. Harris, ed., Plenum Press, NY, Chapter 21 (1992), the disclosures of which are hereby incorporated by reference herein in their entirety.

The linking group used to covalently attach PEG to ADI may be any compatible linking group. In some embodiments the linking group is a biocompatible linking group. As discussed above, "biocompatible" indicates that the compound or group is non-toxic and may be utilized in vitro or in vivo without causing injury, sickness, disease or death. PEG can be bonded to the linking group, for example, via an ether bond, an ester bond, a thiol bond or an amide bond.

Suitable linking groups include, for example, an ester group, an amide group, an imide group, a carbamate group, a carboxyl group, a hydroxyl group, a carbohydrate, a succinimide group (including, for example, succinimidyl succinate (SS), succinimidyl propionate (SPA), succinimidyl carboxymethylate (SCM), succinimidyl succinamide (SSA) or N-hydroxy succinimide (NHS)), an epoxide group, an oxycarbonylimidazole group (including, for example, carbonyldimidazole (CDI)), a nitro phenyl group (including, for example, nitrophenyl carbonate (NPC) or trichlorophenyl carbonate (TPC)), a trysylate group, an aldehyde group, an isocyanate group, a vinylsulfone group, a tyrosine group, a cysteine group, a histidine group or a primary amine. In some embodiments the linking group is an ester group and/or a succinimide group. In some embodiments, the linking group is SS, SPA, SCM, SSA or NHS.

In the present invention, the particular linking groups do not appear to influence the circulating half-life of PEG-ADI or its specific enzyme activity. However, if a linking group is used, in some embodiments it is important to use a biocompatible linking group. The PEG which is attached to the protein may be either a single chain, as with SS-PEG, SPA-PEG and SC-PEG, or a branched chain of PEG may be used, as with PEG2-NHS.

Alternatively, ADI may be coupled directly to PEG (i.e., without a linking group) through an amino group, a sulfhydral group, a hydroxyl group or a carboxyl group. In some embodiments, PEG is coupled to lysine residues on ADI.

ADI-PEG

The attachment of PEG to ADI increases the circulating half-life of ADI. The number of PEG molecules on ADI appears to be related to the circulating half-life of the enzyme, while the amount of retained enzymatic activity appears related to the average molecular weight of the PEG used. Increasing the number of PEG units on ADI decreases the enzymatic activity of the enzyme. Also, it is known that some PEG formulations are difficult to produce and yield relatively low amounts of product. Thus, to achieve an efficacious product, a balance needs to be achieved among circulating half-life, antigenicity, efficiency of production, and enzymatic activity.

Generally, PEG is attached to a primary amine of ADI. Selection of the attachment site of polyethylene glycol on the arginine deiminase is determined by the role of each of the sites within the active domain of the protein, as would be known to the skilled artisan. PEG may be attached to the primary amines of arginine deiminase without substantial loss of enzymatic activity. For example, ADI cloned from *Mycoplasma arginini, Mycoplasma arthritidis* and *Mycoplasma hominis* has about 17 lysines that may be modified by this procedure. In other words, the 17 lysines are all possible points at which ADI can be attached to PEG via a biocompatible linking group, such as SS, SPA, SCM, SSA and/or NHS. PEG may also be attached to other sites on ADI, as would be apparent to one skilled in the art in view of the present disclosure.

From 1 to about 30 PEG molecules may be covalently bonded to ADI. In some embodiments ADI is modified with about 7 to about 15 PEG molecules, from about 9 to about 12 PEG molecules. In other words, about 30% to about 70% of the primary amino groups in arginine deiminase are modified with PEG, about 40% to about 60%, about 45% to about 55%, and about 50% of the primary amino groups in arginine deiminase are modified with PEG. In some embodiments when PEG is covalently bonded to the end terminus of ADI, only 1 PEG molecule is utilized. Increasing the number of PEG units on ADI increases the circulating half life of the enzyme. However, increasing the number of PEG units on ADI decreases the specific activity of the enzyme. Thus, in some embodiments a balance needs to be achieved between the two, as would be apparent to one skilled in the art in view of the present disclosure.

In the present invention, in some embodiments the linking groups attach to a primary amine of arginine deiminase via a maleimide group. Once coupled with arginine deiminase, SS-PEG has an ester linkage next to the PEG, which may render this site sensitive to serum esterase, which may release PEG from ADI in the body. SPA-PEG and PEG2-NHS do not have an ester linkage, so they are not sensitive to serum esterase.

The structural formulas of certain linking groups useful in the present invention are set forth below.

SS-PEG:

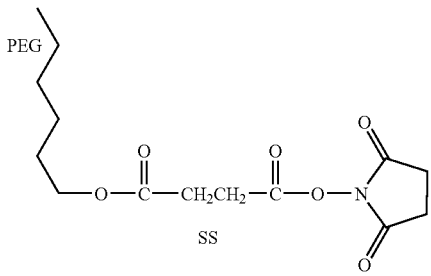

SPA-PEG:

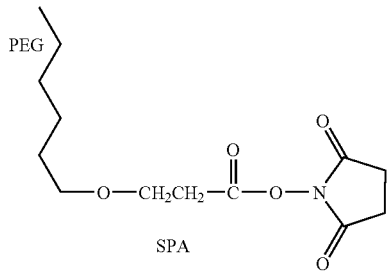

PEG2-NHS

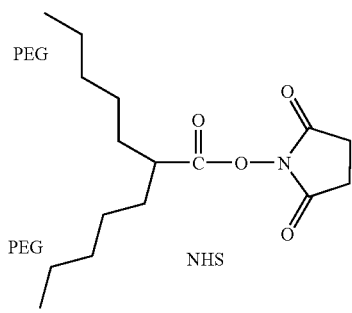

Methods of Treatment

In some embodiments, the present invention provides methods of inhibiting viral replication in an individual comprising administering to said individual a therapeutically or prophylactically effective amount of a compound comprising ADI covalently bonded via a linking group to polyethylene glycol, wherein each polyethylene glycol molecule has an average molecular weight of from about 10,000 to about 30,000. In some embodiments ADI is modified with polyethylene glycol molecules, each molecule having an average molecular weight of about 20,000. In some embodiments the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, a histidine group and combinations thereof. In some embodiments the linking group is succinimidyl succinate. In some embodiments from about 7 to about 15 polyethylene glycol molecules are bonded to arginine deiminase. In some embodiments from about 9 to about 12 polyethylene glycol molecules are bonded to arginine deiminase. In some embodiments the arginine deiminase is derived from a microorganism of the genus *Mycoplasma*. In some embodiments the arginine deiminase is derived from *Mycoplasma arginini, Mycoplasma hominus, Mycoplasma arthritides* and combinations thereof. In some embodiments the virus is HCV. In some embodiments the methods further comprise the step of administering a therapeutically effective amount of an additional anti-viral agent prior to, simultaneously with, or following administration of the arginine deiminase.

A therapeutically effective amount of one of the compounds of the present invention is an amount that is effective to inhibit viral replication. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. The compounds can be administered in one dose, continuously or intermittently throughout the course of treatment. ADI-PEG maybe administered several times each day, once a day, once a week, or once every two weeks.

In some embodiments, ADI-PEG is administered in a weekly dose of at least about 40 IU/m$^2$, at least about 80 IU/m$^2$, at least about 160 IU/m$^2$, or at least about 200 IU/m$^2$. In some embodiments the dose administered lowers plasma levels of arginine to less than about 10, μM, 5 μM, 1 μM, or 100 nM. In some embodiments, ADI-PEG20 is administered in a weekly dose of about 160 IU/m$^2$ resulting in a plasma level in the patient of less than about 5 μM.

The present invention provides methods of inhibiting replication of one or more viruses in an individual comprising administering a therapeutically or prophylactically effective amount of an arginine deiminase bonded to polyethylene glycol to said individual. In some embodiments the virus is a human virus. In some embodiments the virus is HCV. In some embodiments, the individual is infected with two or more different viruses. In some embodiments the two or more viruses are HIV and HCV. In some embodiments the presence and and/or identity of an infecting virus is unknown at or before the time of administration. In some embodiments the methods further comprise the step of administering a therapeutically effective amount of an additional anti-viral agent prior to, simultaneously with, or following administration of the arginine deiminase.

The present invention also provides methods for treating an individual suspected of having been exposed to one or more viruses comprising administering a therapeutically or prophylactically effective amount of an arginine deiminase bonded to polyethylene glycol to said individual. As discussed above, some individuals who have not been diagnosed as being infected with one or more viruses are put in circumstances where it is possible that they could have possibly been exposed to the virus. The treatment of individuals suspected of being exposed to one or more viruses may also include the administration of additional therapeutics as described above. The course of prophylactic treatment may be performed in conjunction with periodic monitoring for indications of viral infection. In some embodiments, following commencement of treatment according to the present invention the individual is diagnosed as being positive for one or more viruses.

In some embodiments the present invention provides methods of inhibiting viral replication in an individual at risk for one or more viruses. The methods comprise administering to the individual an amount of a composition comprising an arginine deiminase bonded to polyethylene glycol effective to inhibit viral replication.

In some embodiments the present invention provides methods of inhibiting viral replication in an individual who has been identified as having been infected with a viral infection. The methods comprise administering to the individual an amount of a composition comprising an arginine deiminase bonded to polyethylene glycol effective to inhibit viral replication.

In some embodiments the composition comprising an arginine deiminase bonded to polyethylene glycol is effective at a concentration of less than 0.1 mM to inhibit viral replication by at least 50% in greater than 50% of cells in an in vitro assay to measure viral replication. In some embodiments the composition comprising an arginine deiminase bonded to polyethylene glycol is effective at a concentration of less than 0.05 mM to inhibit viral replication by at least 50% in greater than 50% of cells in an in vitro assay to measure viral replication. In some embodiments the composition comprising an arginine deiminase bonded to polyethylene glycol is effective at a concentration of less than 0.01 mM to inhibit viral replication by at least 50% in greater than 50% of cells in an in vitro assay to measure viral replication.

In some embodiments the present invention provides methods of concurrently treating a tumor and inhibiting replication of one or more viruses in an individual. The method comprises administering a therapeutically or prophylactically effective amount of an arginine deiminase covalently bonded via a linking group to polyethylene glycol to the individual. In some embodiments the tumor is selected from the group consisting of melanoma, sarcoma, and hepatoma. In some embodiments the tumor is hepatoma and the virus is HCV. In some embodiments, the presence and/or identity of the tumor is unknown at the time of treatment. In some embodiments the presence and/or identity of the virus is unknown at the time of treatment. In some embodiments the methods further comprise administering a therapeutically effective amount of an additional anti-viral agent prior to, simultaneously with, or following administration of the arginine deiminase.

In some embodiments the present invention provides methods for modulating nitric oxide levels in an individual comprising administering a therapeutically or prophylactically effective amount of an arginine deiminase bonded to polyethylene glycol to said individual. In some embodiments, modulation is inhibition of nitric oxide levels. In some embodiments the methods further comprise administering a therapeutically or prophylactically effective amount of an additional anti-viral agent prior to, simultaneously with, or following administration of the arginine deiminase. In some embodiments the individual has been identified as having been infected with one or more viruses.

In some embodiments the present invention provides methods to determine the sensitivity of viral replication to modulating levels of arginine contacting a sample with a composition comprising arginine deiminase bonded to polyethylene glycol and measuring levels of viral RNA or products of viral RNA. Methods of measuring levels of viral RNA or products thereof are well known to those of ordinary skill in the art.

In some embodiments the present invention provides methods of selectively inhibiting viral replication in an individual infected with one or more viruses. The methods comprise administering a therapeutically or prophylactically effective amount of a composition comprising an arginine deiminase bonded to polyethylene glycol to the individual. In some embodiments the virus is HCV. In some embodiments the SI is above 10, above 15, above 20, or above 25.

In some embodiments the present invention provides methods for improving liver function in an individual comprising administering a therapeutically or prophylactically effective amount of a composition comprising arginine deiminase bonded to polyethylene glycol to said individual.

Those of skill in the art are readily able to determine the quality of liver function. In some embodiments, the relative quantity of one or more markers is compared between a healthy patient and a patient with a liver disease or disorder.

In some embodiments, liver function is assessed using the Child-Pugh scale or the Mayo End-stage Liver Disease (MELD) score. The Child-Pugh scale of grading liver function uses several factors to predict mortality in liver disease. Factors considered in the Child Pugh scale include billrubin levels, creatine levels, international normalized ratio (INR; also known as prothrombin time (measure of blood's ability to clot)), presence of ascites in the abdomen, and grade of encephalopathy. Grades are assigned to levels of increasing abnormality of liver function; the grade "A" reflects a Child-Pugh score of 5–6 points and indicates the lowest level of liver abnormality. The grade "B" reflects a Child-Pugh score of 7–9 points and indicates an intermediate level of liver abnormality. The grade "C" reflects a Child-Pugh score of 10–15 points and indicates the highest level of liver abnormality. The MELD scale of grading liver function considers billrubin levels, creatine levels, and international normalized ratio.

In some embodiments the liver function of the individual prior to administration of the arginine deiminase bonded to polyethylene glycol is Child-Pugh level A, level B, or level C.

In some embodiments the present invention provides methods for identifying an individual identified as having one or more viral infections as susceptible to arginine deprivation therapy. The methods comprise obtaining a viral sample from the individual and comparing viral replication in the sample in the presence and absence of a composition comprising arginine deiminase bonded to polyethylene glycol under conditions suitable for viral replication. In some embodiments an inhibition of viral replication of at least 40%, at least 50%, or at least 80% in the sample contacted with ADI-PEG is indicative of an individual who is a candidate for arginine deprivation therapy and an inhibition of viral replication by ADI-PEG of less than 40%, less than 30%, or less than 20% is indicative of an individual who is not a candidate for arginine deprivation therapy.

In some embodiments, the present invention provides methods for treating one or more viral infections in an individual. The methods comprise determining if the individual is a candidate for arginine deprivation therapy as described above and treating the individual with arginine deprivation therapy if the individual is a candidate for arginine deprivation therapy and treating the individual with conventional antiviral treatment if the individual is not a candidate for arginine deprivation therapy.

Methods of determining the most effective means and dosage of administration are well known to those of skill in the art. In some embodiments twice weekly dosing over a period of at least several weeks is used. Often the anti-viral compounds will be administered for extended periods of time and may be administered for the lifetime of the individual. Methods of determining the most effective means and dosage of administration are well known to those of skill in the art. Single or multiple administrations can be carried out with one dose level and pattern being selected by the administrator.

The dosage administered will, of course, vary depending upon known factors, such as the pharmacodynamic characteristics of the particular agent and its mode and route of administration; the age, health and/or weight of the individual; the nature and extent of the symptoms; the kind of concurrent treatment; the frequency of treatment; the symptoms exhibited by the individual, and the effect desired.

Symptoms or criteria for response to anti-viral treatment center around the level of viral replication in the case of most viral infections. Tests for viral circulating viral RNA levels and changes therein are standard and can be applied in cells and animals, including humans. In human patients, tests for liver activities may be performed. One exemplary test is the ALT (Serum Glutamic Pyruvic Transaminase) test. ALT is an enzyme found primarily in the liver but also to a lesser degree, the heart and other tissues, and is useful in diagnosing liver function. The normal adult range for humans is from 0 to about 48 U/L with an optimal adult reading of about 24 U/L. Improvement in one or more of these criteria signals an effective dosage or treatment.

The compounds may be administered in admixture with suitable pharmaceutical diluents, extenders, excipients, or carriers (collectively referred to herein as a pharmaceutically acceptable carrier) selected with respect to the intended form of administration and as consistent with conventional pharmaceutical practices. For example, in some embodiments ADI-PEG may be mixed with a phosphate buffered saline solution, or any other appropriate solution known to those skilled in the art, prior to injection. The ADI-PEG formulation may be administered as a solid (lyophilate) or as a liquid formulation, as desired.

The compositions of the present invention are formulated according to the mode of administration to be used. In cases where pharmaceutical compositions are injectable pharmaceutical compositions, they are sterile, pyrogen free and particulate free. In some embodiments the compositions are isotonic formulations. In some embodiments additives for isotonicity can include one or more of sodium chloride, dextrose, mannitol, sorbitol and lactose. In some embodiments, the compositions are provided as isotonic solutions such as phosphate buffered saline. Stabilizers for the compositions include gelatin and albumin in some embodiments.

The present invention also provides methods of treating a broad spectrum of genetically diverse viruses in a patient comprising administering to the individual a therapeutically effective amount of a compound comprising ADI covalently bonded via a linking group to polyethylene glycol.

Combination Therapy

The compounds of the present invention may additionally be combined with other antiviral compounds to provide a combination therapy. Any known anti-viral may be combined with the compositions of the present invention, as long as the combination does not eliminate the antiviral activity of the compound of ADI-PEG. In the case of HIV a combination therapy of ADI-PEG with AZT, TC-3 or protease inhibitors may be more effective than either agent individually. In the case of hepatitis, a combination of ADI-PEG with one or more of cyclovir, famciclovir or valacyclovir, ribavirin, interferon or beta globulin is administered as a combination therapy. For herpes, a recombinant alpha interferon can be used as a combination therapy with ADI-PEG.

Other anti-viral agents suitable for use in combination therapy are known to the art-skilled and include, without limitation, one or more of AZT (zidovudine, Retrovir), ddI (didanosine, Videx), 3TC (lamivudine, Epivir), d4T (stavudine, Zerit), abacavir (Ziagen), ddC (zalcitabine, Hivid), nevirapine (Viramune), Delavirdine (Rescriptor), indinavir (Crixivan), ritonavir (Norvir), nelfinavir (Viracept), saquinavir, lopinavir/ritonavir (Kaletra), Amprenavir (Agenerase) Atazanavir, tipranavir, fusion inhibitor T-20, Interleukin-2, hydroxyurea, AR177 (Zintevir), fomivirsen sodium (Vitravene), GEM 132, GEM 91, GEM 92, AMD 3100, n-docosanol (1-docosanol), PRO2000, T-1249, T-20, arbidol, SP-303 (Virend), hypericin (VIMRxyn), MDL 28574, SC-48334, ADA, imiquimod (Aldera), ISIS 5320, resiquimod, adefovir dipivoxil (Preveon), DAPD, emtricitabine (Coviracil), entecavir, lamivudine (Zeffix, Epivir-HBV, Heptovir, Heptodin), amantadine (Symmetrel), oseltamivir (Tamiflu), pirodavir, pleconaril (VP-63843), ribavirin (Virazid/Virazide/Virazole), rimantadine (Flumadine), WIN 54954, zanamivir (Relenza), foscamet (Foscavir), maribavir, ABT-378, atevirdine mesylate, calanolide A, capravirine, efavirenz (Sustiva), emivirine (Coactinon), GW420 867X (aka HBY 1293), HBY 097, L-697,661, loviride, MIV-150, PETT-5, R165335-TMC125, talviraline, tivirapine, trovirdine, acyclovir (Zovirax), brivudin (Helpin, Zostrex), cidofovir (Vistide (i.v.); Forvade (topical)), cyclic HPMPC, famciclovir (Famvir), fiacitabine, fialuridine, ganciclovir (Cymvene/Cytovene), GW-273175X, idoxuridine (Herpid, Kerecid/Herplex Liquifilm, Idoxene, Virudox, Iduridin, Stoxil), lobucavir, netivudine (Zonavir), penciclovir (Vectavir/Denavir), sorivudine (Usevir), trifluridine (Viroptic), valaciclovir (Valtrex; Zelitrex), valomaciclovir stearate (MIV-606), vidarabine (Vira-A), 935U83, abacavir (Ziagen/Trizivir), adefovir, adefovir dipivoxil (Preveon), alovudine, AzdU, CS-92, DAPD, didanosine (Videx), dOTC, emtricitabine (Coviracil), fozivudine tidoxil, lamivudine (Epivir/Combivir/Trizivir), lobucavir, lodenosine, stavudine (Zerit), tenofovir (Viread), tenofovir disoproxil fiumarate, zalcitabine (Hivid), zidovudine (Retrovir), A-77003, AG7088, amprenavir (Agenerase), BMS-232632, delavirdine (Rescriptor), DMP-323, DMP-450, GW 433 908, indinavir (Crixivan), KNI-272, lasinavir, lopinavir (Kaletra), Mozenavir, nelfinavir (Viracept), PD178390, ritonavir (Norvir), RPI 312, saquinavir (Invirase/Fortovase), SC-52151, SDZ PRI 053, tipranavir, U-103017, U-96988, Hydroxyurea (Hydrea), AGI549, foscamet (Foscavir), LiGLA, Aciclovir—Valaciclovir, Famciclovir, Idoxuridine, Ganciclovir, Foscarnet, Cidofovir, and Adefovir, enfuvirtide, Valcyte, clevudine, thymalfasin, IL-12, among others.

Combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example in some embodiments treatment with one agent occurs on day 1 and with the other on day 2. The exact regimen will depend on the disease being treated, the severity of the infection and the response to the treatment.

The in vivo means of administration of the compounds of the present invention will vary depending upon the intended application. As one skilled in the art will recognize, administration of the ADI-PEG composition of the present invention can be carried out, for example, by inhalation or suppository or to mucosal tissue such as by lavage to vaginal, rectal, urethral, buccal and sublingual tissue, orally, topically, intranasally, intraperitoneally, parenterally, intravenously, intralymphatically, intratumorly, intramuscularly, interstitially, intra-arterially, subcutaneously, intraoccularly, intrasynovial, transepithelial, and transdermally. The compounds of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, all using dosage forms well known to those of ordinary skill in the pharmaceutical arts.

EXAMPLES

The invention is further demonstrated in the following examples, which are for purposes of illustration, and are not intended to limit the scope of the present invention.

Example 1

Production of Recombinant ADI

Cultures of *Mycoplasma arginini* (ATCC 23243), *Mycoplasma hominis* (ATCC 23114) and *Mycoplasma arthritidis* (ATCC 23192) were obtained from the American Type Culture Collection, Rockville, Md.

Arginine deiminase was cloned from *Mycoplasma arginini*, *Mycoplasma hominis* and *Mycoplasma arthritidis* and expressed in *E. coli* as previously described by S. Misawa et al, J. Biotechnology, 36:145–155 (1994), the disclosure of which is hereby incorporated herein by reference in its entirety. Characterization, by methods known to those skilled in the art, of each of the proteins with respect to specific enzyme activity, $K_m$, $V_{max}$ and pH optima revealed that they were biochemically indistinguishable from each other. The pH optima was determined using a citrate buffer (pH 5–6.5), a phosphate buffer (pH 6.5–7.5) and a borate buffer (pH 7.5–8.5). The $K_m$ and $V_{max}$ were determined by incubating the enzyme with various concentrations of arginine and quantifying citrulline production. The $K_m$ for the various enzymes was about 0.02 to 0.06 µM and the $V_{max}$ was about 15–20 µmol/min/mg, the values of which are within standard error of each other.

The arginine deiminase genes were amplified by polymerase chain reaction using the following primer pair derived from the published sequence of *M. arginini*, as described, for example, by T. Ohno et al, Infect. Immun., 58:3788–3795 (1990), the disclosure of which is hereby incorporated by reference herein in its entirety:

```
                                    (SEQ ID NO:11)
   5'-GCAATCGATGTGTATTTGACAGT-3'

(SEQ ID NO:12)
   5'-TGAGGATCCTTACTACCACTTAACATCTTTACG-3'
```

The polymerase chain reaction product was cloned as a Bam H1-Hind III fragment into expression plasmid pQE16. DNA sequence analysis indicated this fragment had the same sequence for the arginine deiminase gene as described by Ohno et al, Infect. Immun., supra. The five TGA codons in the ADI gene which encode tryptophan in Mycoplasma were changed to TGG codons by oligonucleotide-directed mutagenesis prior to gene expression in *E. coli*, as taught, for example, by J. R. Sayers et al, Biotechniques, 13:592–596 (1992). Recombinant ADI was expressed in inclusion bodies at levels of 10% of total cell protein.

The proteins from each of the above three species of Mycoplasma have approximately 95% homology and are readily purified by column chromatography. Approximately 1.2 g of pure protein may be isolated from 1 liter of fermentation broth. Recombinant ADI is stable for about 2 weeks at 37° C. and for at least 8 months when stored at 4° C. As determined by methods known to those skilled in the art, the proteins had a high affinity for arginine (0.04 µM), and a physiological pH optima of about 7.2 to about 7.4.

Example 2

Renaturation and Purification of Recombinant ADI

ADI protein was renatured, with minor modifications, as described by Misawa et al, J. Biotechnology, 36:145–155 (1994), the disclosure of which is hereby incorporated herein by reference in its entirety. 100 g of cell paste was resuspended in 800 ml of 10 mM K2PO4 pH 7.0, 1 mM EDTA (buffer 1) and the cells were disrupted by two passes in a Microfluidizer (Microfluidics Corporation, Newton, Mass.). Triton X-100 was added to achieve a final concentration of 4% (v/v). The homogenate was stirred for 30 min at 4° C., then centrifuged for 30 min at 13,000 g. The pellet was collected and resuspended in one liter of buffer 1 containing 0.5% Triton X-100. The solution was diafiltered against 5 volumes of denaturation buffer (50 mM Tris HCl, pH 8.5, 10 mM DTT) using hollow-fiber cartridges with 100 kD retention rating (Microgon Inc., Laguna Hills, Calif.). Guanidine HCl was added to achieve a final concentration of 6 M and the solution was stirred for 15 min at 4° C. The solution was diluted 100-fold into refolding buffer 1, 10 mm $K_2PO_4$, pH 7.0 and stirred for 48 hours at 15° C., particulates were removed by centrifugation at 15,000×g.

The resulting supernatant was concentrated on a Q Sepharose Past Flow (Pharmacia Inc., Piscataway, N.J.) column preequilabrated in refolding buffer. ADI was eluted using refolding buffer containing 0.2 M NaCl. The purification procedure yielded ADI protein, which was >95% pure as estimated by SDS-PAGE analysis. Eight g of pure renatured ADI protein was produced from 1 kg of cell paste which corresponds to 200 mg purified ADI per liter of fermentation.

ADI activity was determined by micro-modification of the method described by Oginsky et al, Meth. Enzymol., (1957) 3:639–642. Ten µl samples in 0.1 M $Na_2PO_4$, pH 7.0 (BUN assay buffer) were placed in a 96 well microliter plate, 40 µl of 0.5 mM arginine in BUN assay buffer was added, and the plate was covered and incubated at 37° C. for 15 minutes. Twenty µl of complete BUN reagent (Sigma Diagnostics) was added and the plate was incubated for 10 minutes at 100° C. The plate was then cooled to 22° C. and analyzed at 490 nm by a microliter plate reader (Molecular Devices, Inc). One IU is the amount of enzyme which converts 1 µmole of L-arginine to L-citrulline per minute. Protein concentrations were determined using Pierce Coomassie Blue Protein Assay Reagent (Pierce Co., Rockford, Ill.) with bovine serum albumin as a standard. The enzyme activity of the purified ADI preparations was 17–25 IU/mg.

Example 3

Attachment of PEG to ADI

PEG was covalently bonded to ADI in a 100 mM phosphate buffer, pH 7.4. Briefly, ADI in phosphate buffer was mixed with a 100 molar excess of PEG. The reaction was stirred at room temperature for 1 hour, then the mixture was extensively dialysed to remove unincorporated PEG.

A first experiment was performed where the effect of the linking group used in the PEG-ADI compositions was evaluated. PEG10,000 and ADI were covalently bonded via four different linking groups: an ester group or maleimide group, including SS, SSA, SPA and SSPA, where each PEG molecule had an average molecular weight of 5,000, 10,000, 12,000, 20,000, 30,000 and 40,000; an epoxy group, PEG-epoxy, where each PEG molecule had an average molecular weight of 5,000; and a branched PEG group, PEG2-NHS, where each PEG molecule had an average molecular weight of 10,000, 20,000 and 40,000.

Five IU of the resulting compositions were injected into mice (5 mice in each group). To determine the serum levels of arginine, the mice were bled from the retro orbital plexus (100 µl). Immediately following collection an equal volume of 50% (w/v) of trichloroacetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for citrulline by this method was approximately 2–6 µM and the reproducibility of measurements within about 8%. The amount of serum arginine was determined by amino acid analysis. The linking group covalently bonding the PEG and ADI did not have an appreciable effect on the ability of ADI to reduce serum arginine in vivo.

A second experiment was performed wherein the effect of the linking group and molecular weight of PEG on serum citrulline levels in vivo was evaluated. Mice (5 in each group) were given various compositions of ADI and PEG-ADI in an amount of 5.0 IU. To determine the serum levels of citrulline, the mice were bled from the retro orbital plexus (100 µl). Immediately following collection an equal volume of 50% (w/v) of trichloroacetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for citrulline by this method was approximately 2–6 µM and the reproducibility of measurements within about 8%. The amount of citrulline was determined, and the area under the curve approximated and expressed as µmol days.

The results demonstrate that the molecular weight of the PEG determines the effectiveness of the PEG-ADI composition. The effectiveness of the PEG-ADI compositions does not appear to be based on the method or means of attachment of the PEG to ADI.

The results demonstrate that the optimal molecular weight of PEG is about 20,000. Although PEG30,000 appears to be superior to PEG20,000 in terms of its pharmacodynamics, PEG30,000 is less soluble, which makes it more difficult to work with. The yields, which were based on the recovery of enzyme activity, were about 90% for PEG5,000 and PEG12,000; about 85% for PEG20,000 and about 40% for PEG30,000. Therefore, in some embodiments PEG20,000 appears to be a good compromise between yield and circulating half life, as determined by citrulline production.

In a third experiment, the dose response of serum arginine depletion and the production of citrulline with ADI-SS-PEG5,000 and ADI-SS-PEG20,000 was determined. Mice (5 in each group) were given a single injection of 0.05 IU, 0.5 IU or 5.0 IU of either ADI-SS-PEG5,000 or ADI-SS-PEG20,000. At indicated times, serum was collected, as described above, and an amino acid analysis was performed to quantify serum arginine and serum citrulline. Both formulations induced a dose dependent decrease in serum arginine and an increase in serum citrulline. However, the effects induced by ADI-SS-PEG20,000 were more pronounced and of longer duration than the effects induced by ADI-SS-PEG5,000.

Example 4

Circulating Half-Life

Balb C mice (5 in each group) were injected intravenously with a single 5.0 IU does of either native arginine deiminase or various formulations of arginine deiminase modified with polyethylene glycol. To determine the serum levels of arginine and citrulline, the mice were bled from the retro orbital plexus (100 µl). Immediately following collection an equal volume of 50% (w/v) of trichloro-acetic acid was added. The precipitate was removed by centrifugation (13,000×g for 30 minutes) and the supernatant removed and stored frozen at −70° C. The samples were then analyzed using an automated amino acid analyzer and reagents from Beckman Instruments using protocols supplied by the manufacturer. The limits of sensitivity for arginine by this method was approximately 6 pM and the reproducibility of measurements within about 8%.

A dose dependent decrease in serum arginine levels and a rise in serum citrulline were detected from the single dose administration of native ADI or ADI-SS-PEG. However, the decrease in serum arginine and rise in serum citrulline was short lived, and soon returned to normal. The half-life of arginine depletion is summarized in Table 2 below.

TABLE 2

| Half-Life of Serum Arginine Depletion | |
| --- | --- |
| Compound | Half-Life in Days |
| Native ADI | 1 |
| ADI-SS-PEG5,000 | 5 |
| ADI-SS-PEG12,000 | 15 |
| ADI-SS-PEG20,000 | 20 |
| ADI-SS-PEG30,000 | 22 |

Example 5

Antigenicity of PEG modified ADI

To determine the antigenicity of native ADI, ADI-SS-PEG5,000, and ADI-SS-PEG20,000, the procedures described in, for example, Park, Anticancer Res., supra, and Kamisaki, J. Pharmacol. Exp. Ther., supra, were followed. Briefly, Balb C mice (5 in each group) were intravenously injected weekly for 12 weeks with approximately 0.5 IU (100 µg of protein) of native ADI, ADI-SS-PEG5,000 or ADI-SS-PEG20,000. The animals were bled (0.05 ml) from the retro orbital plexus at the beginning of the experiment and at weeks 4, 8 and 12. The serum was isolated and stored at −70° C. The titers of anti-ADI IgG were determined by ELISA. Fifty μg of ADI was added to each well of a 96 well micro-titer plate and was incubated at room temperature for 4 hours. The plates were rinsed with PBS and then coated with bovine serum albumin (1 mg/ml) to block nonspecific protein binding sites, and stored over night at 4° C. The next day serum from the mice was diluted and added to the wells. After 1 hour the plates were rinsed with PBS and rabbit anti-mouse IgG coupled to peroxidase was added to the wells. The plates were incubated for 30 min and then the resulting UV absorbance was measured using a micro-titer plate reader. The titer was defined as the highest dilution of the serum which resulted in a two-fold increase from background absorbance (approximately 0.50 OD).

ADI-SS-PEG5,000 and ADI-SS-PEG20,000 are significantly less antigenic than native ADI. For example, as few as 4 injections of native ADI resulted in a titer of about $10^6$, while 4 injections of any of the PEG-ADI formulations failed to produce any measurable antibody. However, after 8 injections, the ADI-PEG5,000 had a titer of about $10^2$, while ADI-PEG20,000 did not induce this much of an immune response until after 12 injections. The results demonstrate that attaching PEG to ADI blunts the immune response to the protein.

Example 6

Application to Humans

PEG5,000-ADI and PEG20,000-ADI were incubated ex vivo with normal human serum and the effects on arginine concentration was determined by amino acid analysis, where the enzyme was found to be fully active and capable of degrading all the detectable arginine with the same kinetics as in the experiments involving mice. The reaction was conducted at a volume of 0.1 ml in a time of 1 hour at 37° C.

Additionally, the levels of arginine and citrulline in human serum are identical with that found in mice. PEG-proteins circulate longer in humans than they do in mice. For example, the circulating half life of PEG conjugated adenosine deiminase, asparaginase, glucocerbrocidase, uricase, hemoglobulin and superoxide dismutase all have a circulating half life that is 5 to 10 times longer than the same formulations in mice. What this has meant in the past is that the human dose is most often ⅕ to 1/10 of that used in mice. Accordingly, PEG-ADI should circulate even longer in humans than it does in mice.

Example 7

The antiviral activity of ADI-PEG20 was tested in a stably HCV RNA replicating cell line AVA5 derived by transfection of a human hepatoblastome cell line Huh7 (Blight et al., Efficient Initiation of HCV RNA Replication in Cell Culture, *Science* 2000 290: 1972–1974).

In vitro Replication Assay

A stable HCV RNA replicating cell line AVA5 derived by transfection of a human hepatoblastoma cell line Huh7 was used. Dividing cultures of AVA5 cells were treated once daily for three days (media was changed with each addition of compound) with 4 concentrations of test compound (3 cultures per concentration). A total of 6 untreated control cultures, and triplicate cultures treated with 10, 3, and 1 IU/ml α-interferon (active antiviral with no cytotoxicity), and 100, 10 and 1 uM ribavirin (no antiviral activity and cytotoxic) served as controls. HCV RNA and cellular β-actin RNA levels were assessed 24 hours after the last dose of compound using dot blot hybridization. β-actin RNA levels were used to normalize the amount of cellular RNA in each sample. Toxicity analyses were performed on separate plates from those used for the antiviral assays. Cells for the toxicity analyses were cultured and treated with test compounds with the same schedule and under identical culture conditions as used for the antiviral evaluations. Each compound was tested at 4 concentrations, each in triplicate cultures. Uptake of neutral red dye was used to determine the relative level of toxicity 24 hours following the last treatment. The absorbance of internalized dye at 510 nm ($A_{510}$) was used for the quantitative analysis. Values in test cultures were compared to 9 cultures of untreated cells maintained on the same plate as the test cultures. The 50% and 90% effective antiviral concentrations ($EC_{50}$, $EC_{90}$) and the 50% cytotoxic concentrations ($CC_{50}$) were calculated and used to generate Selectivity Indexes ($CC_{50}/EC_{50}$). An S.I. of 10 or greater is considered to be a selective antiviral effect.

Antiviral activity of ADI-PEG20

A single dose of ADI-PEG20 (0.01 IU/ml) was added to dividing cultures of these cells when they are at 50% confluence. As a control alpha interferon (10 IU/ml) and ribavirin (100 μM) were used as positive controls. After 3 days of treatment RNA was isolated from the cultures using standard laboratory techniques and assayed using dot blots. The amount of HCV mRNA was determined and compared to the mRNA for actin (which is used as a control). The amount of drug (ADI, alpha interferon or raboviron) required to inhibit 50% of the control levels of HCV mRNA is determined. Any dose of drug that causes a 50% inhibition of actin mRNA is considered to have nonspecific inhibitory activity. The results obtained from this experiment are shown below.

| Drug | % inhibition of HCV mRNA | % inhibition of actin |
|---|---|---|
| ADI-PEG20 | 86% | 12% |
| alpha interferon | 92% | 11% |
| ribavirin | 25% | 98% |

These data demonstrate that ADI-PEG inhibits HCV viral replication in vitro nearly as well as alpha interferon and much greater than ribavirin.

Example 8

Dividing cultures of AVA5 cells were treated with various concentrations of PEG-ADI (or in control experiments alpha interferon or ribavirin) for 3 days. HCV mRNA levels were assayed as above. Cell viability was determined using neutral red. The concentrations which inhibit 50% ($IC_{50}$) and 90% ($IC_{90}$) of HCV mRNA levels were determined. The concentration of drug which kills 50% of the cells ($CC_{50}$) was also determined. The $CC_{50}/IC_{50}$ is calculated to determine the selectivity index (SI). An SI>10 is considered to be a selective inhibition of the viral replication. The results are shown below.

| Drug | $CC_{50}$ | $IC_{50}$ | $IC_{90}$ | SI |
|---|---|---|---|---|
| ADI-PEG20 | 0.335 IU/ml | 0.027 IU/ml | 0.188 IU/ml | 12 |
| alpha interferon | >10000 IU/ml | 2.1 IU/ml | 9.0 IU/ml | >4762 |
| ribavirin | 74 µM | >10 µM | >10 µM | NA |

These data confirm that ADI-PEG20 inhibits HCV replication and that this drug is selective.

Example 9

Antiviral Activity and NO Synthesis in Tumor Patients

ADI-PEG 20 was tested for anti-tumor activity in patients with hepatocellular cancer also chronically infected with HCV. Viral titers of HCV in the plasma of these patients using standard clinical assays developed by Hoffman La Roche were also determined. Plasma was obtained prior to treatment with ADI-PEG 20. The patients were injected with 160 IU/m² of ADI-PEG 20 once a week for 3 weeks. One week following the third injection with ADI-PEG 20, plasma was isolated from the patients and again assayed for HCV titer using the same assay. The results from this experiment are shown below.

| Patient Number | HCV titer Pretreatment | HCV titer Post treatment |
|---|---|---|
| 1 | 614,836 | 485,900 |
| 2 | 1,255,542 | 254,729 |
| 3 | 328,134 | 97,535 |
| 4 | 1,466,460 | 63,902 |
| 5 | 1,187,730 | 485,190 |

These data demonstrate that ADI-PEG treatment of humans chronically infected with HCV results in significantly lower titers of HCV in their plasma. Moreover as alpha interferon is only effective in ~50% of these patients and it frequently requires 3–6 months of treatment to achieved a 50% reduction in HCV titers, it appears that ADI-PEG 20 is much more effective in this regard.

ADI-SS PEG 20,000 mw was tested in a Phase 2 study of individuals with inoperable HCC according to Richard Simon statistical design for rapid optimal two-stage Phase 2 testing (Simon R. 1989. Optimal two-stage designs for phase II clinical trials. Control Clin Trials 10:1–10; Simon R M, Steinberg S M, Hamilton M, Hildesheim A, Khleif S, Kwak L W, Mackall C L, Schlom J, Topalian S L, Berzofsky J A. 2001. Clinical trial designs for the early clinical development of therapeutic cancer vaccines. J Clin Oncol 19:1848–1854.). This testing was performed under approval by the Italian Health Ministry at the Pascale National Cancer Institute in Naples, Italy and with the approval of the local institutional review board. All subjects were provided informed consent according to the Declaration of Helsinki. A total of 18 individuals with inoperable HCC were enrolled in this study who were chronically infected with HCV (Izzo submitted). During this study 3 died from progressive disease and failed to receive all 3 cycles of treatment and thus were excluded form further analysis. All remaining 15 subjects received 3 cycles (each consisting of 4 once a week injections) of ADI-SS PEG 20,000 mw at the Optimum Biological Dose. The Optimum Biological Dose was defined as that amount of ADI-SS PEG 20,000 mw which lowered plasma arginine from a resting level of ~130 µM to below the level of detection (<2 µM) for at least 7 days (~160 IU/m²).

The action this therapy had on the tumors was assessed by CT scans once every 4 weeks. Response was defined as either Progressive disease (PD), stable disease (SD), partial response (PR) or complete response (CR) according to standard National Cancer Institute (NCI) criteria. The results from this testing indicated that in the 15 subjects with HCC and HCV the following responses were seen:

| Status of Disease | Number of Subjects |
|---|---|
| Complete Response (CR) | 2 |
| Partial Response (PR) | 7 |
| Stable Disease (SD) | 10 |

None of the subjects had received any systemic anti-tumor treatment (or anti-viral treatment) either prior to or during this study. Clinical laboratory testing was performed at least twice a week during the study and plasma samples were collected once a week and archived frozen at −70° C. It was these frozen archived plasma samples that were later tested for HCV.

Assay for HCV titers and serotyping of human plasma samples

HCV viral titers were determined in the hospital infectious disease clinical laboratory using a standard clinical polymerase-chain-reaction (PCR) assay, Cobas Amplicor HCV Monitor Test, version 2.0; Roche Diagnostics (Germer 1999). The genotype was similarly determined. Viral titers were determined on plasma samples collected prior to ADI-SS PEG 20,000 mw treatment and after 12 weeks of therapy.

NO synthesis

Treatment with ADI-SS PEG 20,000 mw results in a dose dependent decrease in plasma arginine and concomitant decrease in NO synthesis (data not shown). Although this treatment significantly decreased NO levels, there was no measurable effect of this treatment on blood pressure or heart rate.

The following Table 3 lists the effect of ADI-SS PEG 20,000 mw on Hepatitis C Titers and Liver Function Tests.

TABLE 3

Effect of ADI-SS PEG 20,000 mw on Hepatitis C Titers and Liver Function Tests.

| Patient Number | Response | HCV Titer pre Rx | HCV Titer post Rx | Titer % Decrease | Sero Type | ALT Pre Rx | ALT Post Rx | AST Pre Rx | AST Post Rx | Bilirubin Total Pre Rx | Bilirubin Total Post Rx |
|---|---|---|---|---|---|---|---|---|---|---|---|
| 1 | PR | 614,836 | <6000 | >99 | 1b | 271 | 227 | 245 | 182 | 1.16 | 0.92 |
| 2 | SD | 1,466,400 | 63,902 | 96 | 1b | 104 | 115 | 101 | 98 | 0.69 | 0.33 |
| 3 | SD | 269,000 | 28,200 | 90 | 1b | 118 | 81 | 76 | 71 | 1.32 | 0.60 |

TABLE 3-continued

Effect of ADI-SS PEG 20,000 mw on Hepatitis C Titers and Liver Function Tests.

| Patient Number | Response | HCV Titer pre Rx | HCV Titer post Rx | Titer % Decrease | Sero Type | ALT Pre Rx | ALT Post Rx | AST Pre Rx | AST Post Rx | Bilirubin Total Pre Rx | Bilirubin Total Post Rx |
|---|---|---|---|---|---|---|---|---|---|---|---|
| 4 | SD | 1,187,730 | 40,200 | 97 | 1b | 153 | 110 | 145 | 80 | 3.4 | 0.45 |
| 5 | PR | 614836 | 40,200 | 93 | 1b | 87 | 122 | 85 | 108 | 1.8 | 0.45 |
| 6 | CR | 328,134 | 173,000 | 47 | 1b | 63 | 66 | 51 | 47 | 0.94 | 0.45 |
| 7 | CR | <6000 | <6000 | — | 1b | 57 | 67 | 65 | 74 | 1.72 | 0.45 |
| 8 | SD | 676,000 | 120,000 | 82 | 1b | 57 | 67 | 65 | 74 | 1.72 | 0.45 |
| 9 | SD | <6000 | <6000 | — | 1b | 63 | 25 | 37 | 14 | 1.73 | 0.60 |
| 10 | PR | 1,950,000 | 921,000 | 53 | 1b | 68 | 58 | 69 | 47 | 1.70 | 0.73 |
| 11 | SD | 386,000 | 331,000 | 14 | 1b | 89 | 153 | 95 | 151 | 2.83 | 3.1 |
| 12 | PR | 2,830,000 | 3,390,000 | increase | 1b | 77 | 65 | 85 | 83 | 0.72 | 0.83 |
| 13 | SD | 689,000 | 1,010,000 | increase | 2c | 66 | 54 | 68 | 47 | 1.66 | 0.99 |
| 14 | SD | 351,000 | 690,000 | increase | 2c | 115 | 137 | 111 | 152 | 3.13 | 3.1 |
| 15 | SD | 801,000 | 1,210,000 | increase | 2c | 79 | 87 | 85 | 76 | 1.68 | 1.80 |

Note
All post RX values are after 3 cycles at the OBD.

Each of the patents, Genbank accession numbers, patent applications and publications described herein are hereby incorporated by reference herein in their entirety.

Various modifications of the invention, in addition to those described herein, will be apparent to one skilled in the art in view of the foregoing description. Such modifications are also intended to fall within the scope of the appended claims.

What is claimed is:

1. A method of inhibiting the replication of HCV serotype 1b or 2a/2c in an individual comprising administering to said individual a composition comprising an arginine deiminase bonded to polyethylene glycol in an amount effective to inhibit the replication of HCV serotype 1b or 2a/2c in said individual.

2. The method of claim 1 further comprising the step of administering to said individual one or more compounds selected from the group consisting of antibiotics, anti-virals, antifungals, and anti-protozoan drugs.

3. The method of claim 1 further comprising the step of administering to said individual one or more other anti-viral compounds.

4. The method of claim 2 wherein said anti-viral compounds are one or more of azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), delavirdine (Rescriptor), pegylated (PEG) interferon-α (IFN), or ribavirin.

5. The method of claim 1 wherein said composition is administered intramuscularly, intradermally, or intraperitoneally.

6. The method of claim 1 wherein said composition comprising an arginine deiminase bonded to polyethylene glycol is effective at a concentration of less than about 1 mM to inhibit viral replication by at least 50%.

7. The method of claim 1 wherein the amount of arginine deiminase bonded to polyethylene glycol effective to inhibit viral replication is between about 40 IU/m$^2$ and about 160 IU/m$^2$ per week.

8. The method of claim 1 wherein the amount of arginine deiminase bonded to polyethylene glycol effective to inhibit viral replication is about 160 IU/m² per week.

9. The method of claim 1 wherein the amount of arginine deiminase bonded to polyethylene glycol effective to inhibit viral replication lowers plasma arginine levels to less than 5 µM.

10. The method of claim 1 wherein the arginine deiminase is covalently bonded via a linking group to polyethylene glycol, wherein each of said polyethylene glycol molecules has a molecular weight of about 10,000 to about 30,000.

11. The method of claim 1 wherein each of said polyethylene glycol molecules has a molecular weight of about 20,000.

12. The method of claim 10 wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, and a histidine group, and combinations thereof.

13. The method of claim 10 wherein the linking group is succinimidyl succinate.

14. The method of claim 1 wherein said arginine deiminase is derived from a microorganism of the genus *Mycoplasma*.

15. The method of claim 14 wherein said microorganism is selected from the group consisting of *Mycoplasma arginini, Mycoplasma hominis, Mycoplasma arthritidis* and combinations thereof.

16. The method of claim 1 wherein the arginine deiminase has an amino acid sequence of SEQ ID NO: 1, 2, 3, 4, 5, 6, 7, 8, 9, 10, 13, 14, 15, 16, 17, 18, 19, 20 or 21.

17. The method of claim 1 wherein the arginine deiminase has an amino acid sequence of SEQ ID NO: 1 or 4.

18. The method of claim 1 wherein the virus is HCV serotype 1b.

19. A method of inhibiting the replication of HCV serotype 1b or 2a/2c in an individual who has been infected with HCV comprising administering to said individual an amount of a composition comprising an arginine deiminase bonded to polyethylene glycol effective to inhibit the replication of HCV serotype 1b or 2a/2c in said individual.

20. The method of any one of claims 2 or 3 wherein said compound is administered to said individual simultaneously with the administration of said composition comprising arginine deiminase bonded to polyethylene glycol.

21. A method of selectively inhibiting the replication of HCV serotype 1b or 2a/2c in an individual in need thereof comprising administering a therapeutically or prophylactically effective amount of a composition comprising an arginine deiminase bonded to polyethylene glycol to said individual.

22. The method of claim 3 wherein the one or more additional antiviral compounds are selected from the group consisting of cyclovir, famciclovir, valacyclovir, ribavirin, interferon or beta globulin.

23. A method of reducing HCV serotype 1b or 2a/2c viral titer in an individual comprising administering to said individual a composition comprising an arginine deiminase bonded to polyethylene glycol in an amount effective to reduce HCV serotype 1b or 2a/2c viral titer in said individual.

24. The method of claim 23 further comprising the step of administering to said individual one or more additional antiviral compounds.

25. The method of claim 23 wherein said composition is administered intramuscularly, intradermally, or intraperitoneally.

26. The method of claim 23 wherein said composition comprising an arginine deiminase bonded to polyethylene glycol is effective at a concentration of less than 1 mM to reduce HCV viral titer by at least 50%.

27. The method of claim 23 wherein the amount of arginine deiminase bonded to polyethylene glycol effective to reduce HCV viral titer is between about 40 IU/m² and about 160 IU/m² per week.

28. The method of claim 23 wherein the amount of arginine deiminase bonded to polyethylene glycol effective to reduce HCV viral titer is about 160 IU/m² per week.

29. The method of claim 23 wherein the amount of arginine deiminase bonded to polyethylene glycol effective to reduce HCV viral titer lowers plasma arginine levels to less than 5 µM.

30. The method of claim 23 wherein the arginine deiminase is covalently bonded via a linking group to polyethylene glycol, wherein each of said polyethylene glycol molecules has a molecular weight of about 10,000 to about 30,000.

31. The method of claim 23 wherein each of said polyethylene glycol molecules has a molecular weight of about 20,000.

32. The method of claim 30 wherein the linking group is selected from the group consisting of a succinimide group, an amide group, an imide group, a carbamate group, an ester group, an epoxy group, a carboxyl group, a hydroxyl group, a carbohydrate, a tyrosine group, a cysteine group, and a histidine group, and combinations thereof.

33. The method of claim 30 wherein the linking group is succinimidyl succinate.

34. The method of claim 23 wherein said arginine deiminase is derived from a microorganism of the genus *Mycoplasma*.

35. The method of claim 34 wherein said microorganism is selected from the group consisting of *Mycoplasma arginini, Mycoplasma hominis, Mycoplasma arthritidis* and combinations thereof.

36. The method of claim 23 wherein the arginine deiminase has an amino acid sequence of SEQ ID NO: 1, 2, 3, 4, 5, 6, 7, 8, 9, 10, 13, 14, 15, 16, 17, 18, 19, 20 or 21.

37. The method of claim 23 wherein the arginine deiminase has an amino acid sequence of SEQ ID NO: 1 or 4.

38. The method of claim 23 wherein the virus is HCV serotype 1b.

39. The method of claim 24 wherein the one or more conventional antiviral medicaments are selected from the group consisting of cyclovir, famciclovir, valacyclovir, ribavirin, interferon or beta globulin.

40. The method of claim 23 wherein the amount of arginine deiminase bonded to polyethylene glycol administered to the individual is about 200 IU/m² per week.

41. The method of claim 1 wherein the amount of arginine deiminase bonded to polyethylene glycol administered to the individual is about 200 IU/m² per week.

* * * * *

SEQUENCE LISTING

<160> NUMBER OF SEQ ID NOS: 21

<210> SEQ ID NO 1
<211> LENGTH: 409
<212> TYPE: PRT
<213> ORGANISM: Mycoplasma hominus

<400> SEQUENCE: 1

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160
```

```
Pro Phe Ala Ser Val Gly Asn Gly Val Thr Ile His Phe Met Arg Tyr
                165                 170                 175
Ile Val Arg Arg Arg Glu Thr Leu Phe Ala Arg Phe Val Phe Arg Asn
                180                 185                 190
His Pro Lys Leu Val Lys Thr Pro Trp Tyr Tyr Asp Pro Ala Met Lys
                195                 200                 205
Met Pro Ile Glu Gly Gly Asp Val Phe Ile Tyr Asn Asn Glu Thr Leu
            210                 215                 220
Val Val Gly Val Ser Glu Arg Thr Asp Leu Asp Thr Ile Thr Leu Leu
225                 230                 235                 240
Ala Lys Asn Ile Lys Ala Asn Lys Glu Val Glu Phe Lys Arg Ile Val
                245                 250                 255
Ala Ile Asn Val Pro Lys Trp Thr Asn Leu Met His Leu Asp Thr Trp
                260                 265                 270
Leu Thr Met Leu Asp Lys Asn Lys Phe Leu Tyr Ser Pro Ile Ala Asn
            275                 280                 285
Asp Val Phe Lys Phe Trp Asp Tyr Asp Leu Val Asn Gly Gly Ala Glu
            290                 295                 300
Pro Gln Pro Gln Leu Asn Gly Leu Pro Leu Asp Lys Leu Leu Ala Ser
305                 310                 315                 320
Ile Ile Asn Lys Glu Pro Val Leu Ile Pro Ile Gly Ala Gly Ala
                325                 330                 335
Thr Glu Met Glu Ile Ala Arg Glu Thr Asn Phe Asp Gly Thr Asn Tyr
            340                 345                 350
Leu Ala Ile Lys Pro Gly Leu Val Ile Gly Tyr Asp Arg Asn Glu Lys
                355                 360                 365
Thr Asn Ala Ala Leu Lys Ala Ala Gly Ile Thr Val Leu Pro Phe His
            370                 375                 380
Gly Asn Gln Leu Ser Leu Gly Met Gly Asn Ala Arg Cys Met Ser Met
385                 390                 395                 400
Pro Leu Ser Arg Lys Asp Val Lys Trp
                405

<210> SEQ ID NO 2
<211> LENGTH: 409
<212> TYPE: PRT
<213> ORGANISM: Mycoplasma hominus

<400> SEQUENCE: 2

Met Ser Val Phe Asp Ser Lys Phe Asn Gly Ile His Val Tyr Ser Glu
1               5                   10                  15
Ile Gly Glu Leu Glu Thr Val Leu Val His Glu Pro Gly Arg Glu Ile
                20                  25                  30
Asp Tyr Ile Thr Pro Ala Arg Leu Asp Glu Leu Leu Phe Ser Ala Ile
            35                  40                  45
Leu Glu Ser His Asp Ala Arg Lys Glu His Gln Ser Phe Val Lys Ile
        50                  55                  60
Met Lys Asp Arg Gly Ile Asn Val Val Glu Leu Thr Asp Leu Val Ala
65                  70                  75                  80
Glu Thr Tyr Asp Leu Ala Ser Lys Ala Ala Lys Glu Glu Phe Ile Glu
                85                  90                  95
Thr Phe Leu Glu Glu Thr Val Pro Val Leu Thr Glu Ala Asn Lys Glu
            100                 105                 110
Ala Val Arg Ala Phe Leu Leu Ser Lys Pro Thr His Glu Met Val Glu
        115                 120                 125
```

```
Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Pro Ile Glu Gly Gly Asp Val Phe Ile Tyr Asn Asn Glu Thr Leu
    210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 3
<211> LENGTH: 409
<212> TYPE: PRT
<213> ORGANISM: Mycoplasma hominus

<400> SEQUENCE: 3

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95
```

```
Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Ser Ile Glu Gly Gly Asp Val Phe Ile Tyr Asn Asn Glu Thr Leu
    210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 4
<211> LENGTH: 409
<212> TYPE: PRT
<213> ORGANISM: Mycoplasma hominus

<400> SEQUENCE: 4

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60
```

```
Met Lys Asp Arg Gly Ile Asn Val Val Glu Leu Thr Asp Leu Val Ala
 65                  70                  75                  80

Glu Thr Tyr Asp Leu Ala Ser Lys Ala Ala Lys Glu Glu Phe Ile Glu
             85                  90                  95

Thr Phe Leu Glu Glu Thr Val Pro Val Leu Thr Glu Ala Asn Lys Glu
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Ser Ile Glu Gly Gly Asp Val Phe Ile Tyr Asn Asn Glu Thr Leu
    210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405
```

<210> SEQ ID NO 5
<211> LENGTH: 410
<212> TYPE: PRT
<213> ORGANISM: Mycoplasma arginini

<400> SEQUENCE: 5

```
Met Ser Val Phe Asp Ser Lys Phe Lys Gly Ile His Val Tyr Ser Glu
 1               5                  10                  15

Ile Gly Glu Leu Glu Ser Val Leu Val His Glu Pro Gly Arg Glu Ile
            20                  25                  30
```

```
Asp Tyr Ile Thr Pro Ala Arg Leu Asp Glu Leu Leu Phe Ser Ala Ile
            35                  40                  45
Leu Glu Ser His Asp Ala Arg Lys Glu His Lys Gln Phe Val Ala Glu
     50                  55                  60
Leu Lys Ala Asn Asp Ile Asn Val Val Glu Leu Ile Asp Leu Val Ala
 65                  70                  75                  80
Glu Thr Tyr Asp Leu Ala Ser Gln Glu Ala Lys Asp Lys Leu Ile Glu
                 85                  90                  95
Glu Phe Leu Glu Asp Ser Glu Pro Val Leu Ser Glu Glu His Lys Val
            100                 105                 110
Val Val Arg Asn Phe Leu Lys Ala Lys Lys Thr Ser Arg Lys Leu Val
        115                 120                 125
Glu Ile Met Met Ala Gly Ile Thr Lys Tyr Asp Leu Gly Ile Glu Ala
    130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
            180                 185                 190
Asn His Pro Lys Leu Ile Asn Thr Pro Trp Tyr Tyr Asp Pro Ser Leu
        195                 200                 205
Lys Leu Ser Ile Glu Gly Gly Asp Val Phe Ile Tyr Asn Asn Asp Thr
    210                 215                 220
Leu Val Val Gly Val Ser Glu Arg Thr Asp Leu Gln Thr Val Thr Leu
225                 230                 235                 240
Leu Ala Lys Asn Ile Val Ala Asn Lys Glu Cys Glu Phe Lys Arg Ile
                245                 250                 255
Val Ala Ile Asn Val Pro Lys Trp Thr Asn Leu Met His Leu Asp Thr
            260                 265                 270
Trp Leu Thr Met Leu Asp Lys Asp Lys Phe Leu Tyr Ser Pro Ile Ala
        275                 280                 285
Asn Asp Val Phe Lys Phe Trp Asp Tyr Asp Leu Val Asn Gly Gly Ala
    290                 295                 300
Glu Pro Gln Pro Val Glu Asn Gly Leu Pro Leu Glu Gly Leu Leu Gln
305                 310                 315                 320
Ser Ile Ile Asn Lys Lys Pro Val Leu Ile Pro Ile Ala Gly Glu Gly
                325                 330                 335
Ala Ser Gln Met Glu Ile Glu Arg Glu Thr His Phe Asp Gly Thr Asn
            340                 345                 350
Tyr Leu Ala Ile Arg Pro Gly Val Val Ile Gly Tyr Ser Arg Asn Glu
        355                 360                 365
Lys Thr Asn Ala Ala Leu Glu Ala Ala Gly Ile Lys Val Leu Pro Phe
    370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 6
<211> LENGTH: 410
<212> TYPE: PRT
<213> ORGANISM: Mycoplasma arginini
```

```
<400> SEQUENCE: 6

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Glu Val
                100                 105                 110

Val Val Arg Asn Phe Leu Lys Ala Lys Lys Thr Ser Arg Lys Leu Val
            115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
            195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410
```

<210> SEQ ID NO 7
<211> LENGTH: 409
<212> TYPE: PRT
<213> ORGANISM: Mycoplasma arthritidis

<400>

-continued

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 8
<211> LENGTH: 409
<212> TYPE: PRT
<213> ORGANISM: Mycoplasma arthritidis

<400> SEQUENCE: 8

Met Ser Val Phe Asp Ser Lys Phe Lys Gly Ile His Val Tyr Ser Glu
1               5 10 15

Ile Gly Glu Leu Glu Ser Val Leu Val His Glu Pro Gly Arg Glu Ile
20 25 30

Asp Tyr Ile Thr Pro Ala Arg Leu Asp Glu Leu Leu Phe Ser Ala Ile
35 40 45

Leu Glu Ser His Asp Ala Arg Lys Glu Gln Ser Gln Phe Val Ala Ile
50 55 60

Leu Lys Ala Asn Asp Ile Asn Val Val Glu Thr Ile Asp Leu Val Ala
65 70 75 80

Glu Thr Tyr Asp Leu Ala Ser Gln Glu Ala Lys Asp Arg Leu Ile Glu
85 90 95

Glu Phe Leu Glu Asp Ser Glu Pro Val Leu Ser Glu Ala His Glu Glu
100 105 110

Val Val Arg Asn Phe Leu Lys Ala Lys Lys Thr Ser Arg Lys Leu Val
115 120 125

Glu Leu Met Met Ala Gly Ile Thr Lys Tyr Asp Leu Gly Val Glu Ala
130 135 140

Asp His Glu Leu Ile Val Asp Pro Met Pro Asn Leu Tyr Phe Thr Arg
145 150 155 160

Asp Pro Phe Ala Ser Val Gly Asn Gly Val Thr Ile His Phe Met Arg
165 170 175

Tyr Ile Val Arg Arg Arg Glu Thr Leu Phe Ser Arg Phe Val Phe Arg
180 185 190

Asn His Pro Lys Leu Val Asn Thr Pro Trp Tyr Tyr Asp Pro Ala Met
195 200 205

Lys Leu Ser Ile Glu Gly Gly Asp Val Phe Ile Tyr Asn Asn Asp Thr
210 215 220

Leu Val Val Gly Val Ser Glu Arg Thr Asp Leu Asp Thr Val Thr Leu
225 230 235 240

Leu Ala Lys Asn Leu Val Ala Asn Lys Glu Cys Glu Phe Lys Arg Ile
245 250 255

Val Ala Ile Asn Val Pro Lys Trp Thr Asn Leu Met His Leu Asp Ile
260 265 270

Trp Leu Thr Met Leu Asp Lys Asn Lys Phe Leu Tyr Ser Pro Ile Ala
275 280 285

Asn Asp Val Phe Lys Phe Trp Asp Tyr Asp Leu Val Asn Gly Gly Ala
290 295 300

Glu Pro Gln Pro Val Glu Asn Gly Leu Pro Leu Glu Lys Leu Leu Gln
305 310 315 320

Ser Ile Ile Asn Lys Lys Pro Val Leu Ile Pro Ile Ala Gly Glu Gly
325 330 335

Ala Ser Gln Met Glu Ile Glu Arg Glu Thr His Phe Asp Gly Thr Asn
340 345 350

```
Tyr Ile Ala Ile Arg Pro Gly Val Val Ile Gly Tyr Ser Arg Asn Glu
        355                 360                 365

Lys Thr Asn Ala Ala Leu Lys Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 9
<211> LENGTH: 409
<212> TYPE: PRT
<213> ORGANISM: Mycoplasma arthritidis

<400> SEQUENCE: 9

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu Gln Ser Gln Phe Val Ala Ile
    50                  55                  60

Leu Lys Ala Asn Asp Ile Asn Val Val Glu Thr Ile Asp Leu Val Ala
65                  70                  75                  80

Glu Thr Tyr Asp Leu Ala Ser Gln Glu Ala Lys Asp Arg Leu Ile Glu
                85                  90                  95

Glu Phe Leu Glu Asp Ser Glu Pro Val Leu Ser Glu Ala His Glu Lys
            100                 105                 110

Val Val Arg Asn Phe Leu Lys Ala Lys Lys Thr Ser Arg Lys Leu Val
        115                 120                 125

Glu Leu Met Met Ala Gly Ile Thr Lys Tyr Asp Leu Gly Val Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Ile Val Arg Arg Glu Thr Leu Phe Ser Arg Phe Val Phe Arg
            180                 185                 190

Asn His Pro Lys Leu Val Asn Thr Pro Trp Tyr Asp Pro Ala Met
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Asp Thr Val Thr Leu
225                 230                 235                 240

Leu Ala Lys Asn Leu Val Ala Asn Lys Glu Cys Glu Phe Lys Arg Ile
                245                 250                 255

Val Ala Ile Asn Val Pro Lys Trp Thr Asn Leu Met His Leu Asp Ile
            260                 265                 270

Trp Leu Thr Met Leu Asp Lys Asn Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Lys Leu Leu Gln
305                 310                 315                 320
```

```
Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
                340                 345                 350

Tyr Ile Ala Ile Arg Pro Gly Val Val Ile Gly Tyr Ser Arg Asn Glu
                355                 360                 365

Lys Thr Asn Ala Ala Leu Lys Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 10
<211> LENGTH: 409
<212> TYPE: PRT
<213> ORGANISM: Mycoplasma arthritidis

<400> SEQUENCE: 10

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu Gln Ser Gln Phe Val Ala Ile
        50                  55                  60

Leu Lys Ala Asn Asp Ile Asn Val Val Glu Thr Ile Asp Leu Val Ala
65                  70                  75                  80

Glu Thr Tyr Asp Leu Ala Ser Gln Glu Ala Lys Asp Arg Leu Ile Glu
                85                  90                  95

Glu Phe Leu Glu Asp Ser Glu Pro Val Leu Ser Glu Ala His Lys Glu
                100                 105                 110

Val Val Arg Asn Phe Leu Lys Ala Lys Lys Thr Ser Arg Lys Leu Val
                115                 120                 125

Glu Leu Met Met Ala Gly Ile Thr Lys Tyr Asp Leu Gly Val Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Ile Val Arg Arg Arg Glu Thr Leu Phe Ser Arg Phe Val Phe Arg
                180                 185                 190

Asn His Pro Lys Leu Val Asn Thr Pro Trp Tyr Tyr Asp Pro Ala Met
                195                 200                 205

Lys Leu Ser Ile Glu Gly Gly Asp Val Phe Ile Tyr Asn Asn Asp Thr
        210                 215                 220

Leu Val Val Gly Val Ser Glu Arg Thr Asp Leu Asp Thr Val Thr Leu
225                 230                 235                 240

Leu Ala Lys Asn Leu Val Ala Asn Lys Glu Cys Glu Phe Lys Arg Ile
                245                 250                 255

Val Ala Ile Asn Val Pro Lys Trp Thr Asn Leu Met His Leu Asp Ile
                260                 265                 270

Trp Leu Thr Met Leu Asp Lys Asn Lys Phe Leu Tyr Ser Pro Ile Ala
        275                 280                 285
```

-continued

```
Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Lys Leu Leu Gln
305                 310                 315                 320

Ser Ile Ile Asn Lys Lys Pro Val Leu Ile Pro Ile Ala Gly Glu Gly
            325                 330                 335

Ala Ser Gln Met Glu Ile Glu Arg Glu Thr His Phe Asp Gly Thr Asn
            340                 345                 350

Tyr Ile Ala Ile Arg Pro Gly Val Val Ile Gly Tyr Ser Arg Asn Glu
        355                 360                 365

Lys Thr Asn Ala Ala Leu Lys Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys
                405
```

<210> SEQ ID NO 11
<211> LENGTH: 23
<212> TYPE: DNA
<213> ORGANISM: Artificial Sequence
<220> FEATURE:
<223> OTHER INFORMATION: oligonucleotide

<400> SEQUENCE: 11
gcaatcgatg tgtatttgac agt    23

<210> SEQ ID NO 12
<211> LENGTH: 33
<212> TYPE: DNA
<213> ORGANISM: Artificial Sequence
<220> FEATURE:
<223> OTHER INFORMATION: oligonucleotide

<400> SEQUENCE: 12
tgaggatcct tactaccact taacatcttt acg    33

<210> SEQ ID NO 13
<211> LENGTH: 411
<212> TYPE: PRT
<213> ORGANISM: Streptococcus pyogenes

<400> SEQUENCE: 13

```
Met Thr Ala Gln Thr Pro Ile His Val Tyr Ser Glu Ile Gly Lys Leu
1               5                   10                  15

Lys Lys Val Leu Leu His Arg Pro Gly Lys Glu Ile Glu Asn Leu Met
            20                  25                  30

Pro Asp Tyr Leu Glu Arg Leu Leu Phe Asp Asp Ile Pro Phe Leu Glu
        35                  40                  45

Asp Ala Gln Lys Glu His Asp Ala Phe Ala Gln Ala Leu Arg Asp Glu
    50                  55                  60

Gly Ile Glu Val Leu Tyr Leu Glu Thr Leu Ala Ala Glu Ser Leu Val
65                  70                  75                  80

Thr Pro Glu Ile Arg Glu Ala Phe Ile Asp Glu Tyr Leu Ser Glu Ala
                85                  90                  95

Asn Ile Arg Gly Arg Ala Thr Lys Lys Ala Ile Arg Glu Leu Leu Met
            100                 105                 110

Ala Ile Glu Asp Asn Gln Glu Leu Ile Glu Lys Thr Met Ala Gly Val
        115                 120                 125
```

-continued

```
Gln Lys Ser Glu Leu Pro Glu Ile Pro Ala Ser Glu Lys Gly Leu Thr
130                 135                 140

Asp Leu Val Glu Ser Asn Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175

Leu Asn His Met Phe Ser Glu Thr Arg Asn Arg Glu Thr Leu Tyr Gly
            180                 185                 190

Lys Tyr Ile Phe Thr His His Pro Ile Tyr Gly Gly Lys Val Pro
        195                 200                 205

Met Val Tyr Asp Arg Asn Glu Thr Thr Arg Ile Glu Gly Gly Asp Glu
    210                 215                 220

Leu Val Leu Ser Lys Asp Val Leu Ala Val Gly Ile Ser Gln Arg Thr
225                 230                 235                 240

Asp Ala Ala Ser Ile Glu Lys Leu Leu Val Asn Ile Phe Lys Gln Asn
                245                 250                 255

Leu Gly Phe Lys Lys Val Leu Ala Phe Glu Phe Ala Asn Asn Arg Lys
            260                 265                 270

Phe Met His Leu Asp Thr Val Phe Thr Met Val Asp Tyr Asp Lys Phe
        275                 280                 285

Thr Ile His Pro Glu Ile Glu Gly Asp Leu Arg Val Tyr Ser Val Thr
    290                 295                 300

Tyr Asp Asn Glu Glu Leu His Ile Val Glu Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Tyr Asn
        355                 360                 365

Arg Asn Thr Ile Thr Asn Ala Ile Leu Glu Ser Lys Gly Leu Lys Leu
    370                 375                 380

Ile Lys Ile His Gly Ser Glu Leu Val Arg Gly Arg Gly Gly Pro Arg
385                 390                 395                 400

Cys Met Ser Met Pro Phe Glu Arg Glu Asp Ile
                405                 410
```

<210> SEQ ID NO 14
<211> LENGTH: 409
<212> TYPE: PRT
<213> ORGANISM: Streptococcus pneumoniae

<400> SEQUENCE: 14

```
Met Ser Ser His Pro Ile Gln Val Phe Ser Glu Ile Gly Lys Leu Lys
1               5                   10                  15

Lys Val Met Leu His Arg Pro Gly Lys Glu Leu Glu Asn Leu Leu Pro
            20                  25                  30

Asp Tyr Leu Glu Arg Leu Leu Phe Asp Asp Ile Pro Phe Leu Glu Asp
        35                  40                  45

Ala Gln Lys Glu His Asp Ala Phe Ala Gln Ala Leu Arg Asp Glu Gly
    50                  55                  60

Ile Glu Val Leu Tyr Leu Glu Gln Leu Ala Ala Glu Ser Leu Thr Ser
65                  70                  75                  80

Pro Glu Ile Arg Asp Gln Phe Ile Glu Glu Tyr Leu Asp Glu Ala Asn
                85                  90                  95
```

```
Ile Arg Asp Arg Gln Thr Lys Val Ala Ile Arg Glu Leu Leu His Gly
            100                 105                 110

Ile Lys Asp Asn Gln Glu Leu Val Glu Lys Thr Met Ala Gly Ile Gln
        115                 120                 125

Lys Val Glu Leu Pro Glu Ile Pro Asp Glu Ala Lys Asp Leu Thr Asp
130                 135                 140

Leu Val Glu Ser Glu Tyr Pro Phe Ala Ile Asp Pro Met Pro Asn Leu
145                 150                 155                 160

Tyr Phe Thr Arg Asp Pro Phe Ala Thr Ile Gly Asn Ala Val Ser Leu
                165                 170                 175

Asn His Met Phe Ala Asp Thr Arg Asn Arg Glu Thr Leu Tyr Gly Lys
            180                 185                 190

Tyr Ile Phe Lys Tyr His Pro Ile Tyr Gly Gly Lys Val Asp Leu Val
        195                 200                 205

Tyr Asn Arg Glu Glu Asp Thr Arg Ile Glu Gly Gly Asp Glu Leu Val
210                 215                 220

Leu Ser Lys Asp Val Leu Ala Val Gly Ile Ser Gln Arg Thr Asp Ala
225                 230                 235                 240

Ala Ser Ile Glu Lys Leu Leu Val Asn Ile Phe Lys Lys Asn Val Gly
                245                 250                 255

Phe Lys Lys Val Leu Ala Phe Glu Phe Ala Asn Asn Arg Lys Phe Met
            260                 265                 270

His Leu Asp Thr Val Phe Thr Met Val Asp Tyr Asp Lys Phe Thr Ile
        275                 280                 285

His Pro Glu Ile Glu Gly Asp Leu His Val Tyr Ser Val Thr Tyr Glu
290                 295                 300

Asn Glu Lys Leu Lys Ile Val Glu Glu Lys Gly Asp Leu Ala Glu Leu
305                 310                 315                 320

Leu Ala Gln Asn Leu Gly Val Glu Lys Val His Leu Ile Arg Cys Gly
                325                 330                 335

Gly Gly Asn Ile Val Ala Ala Arg Glu Gln Trp Asn Asp Gly Ser
            340                 345                 350

Asn Thr Leu Thr Ile Ala Pro Gly Val Val Val Tyr Asp Arg Asn
        355                 360                 365

Thr Val Thr Asn Lys Ile Leu Glu Glu Tyr Gly Leu Arg Leu Ile Lys
370                 375                 380

Ile Arg Gly Ser Glu Leu Val Arg Gly Arg Gly Pro Arg Cys Met
385                 390                 395                 400

Ser Met Pro Phe Glu Arg Glu Val
                405
```

<210> SEQ ID NO 15
<211> LENGTH: 410
<212> TYPE: PRT
<213> ORGANISM: Borrelia burgdorferi

<400> SEQUENCE: 15

```
Met Glu Glu Glu Tyr Leu Asn Pro Ile Asn Ile Phe Ser Glu Ile Gly
1               5                   10                  15

Arg Leu Lys Lys Val Leu Leu His Arg Pro Gly Glu Glu Leu Glu Asn
            20                  25                  30

Leu Thr Pro Leu Ile Met Lys Asn Phe Leu Phe Asp Asp Ile Pro Tyr
        35                  40                  45

Leu Lys Val Ala Arg Gln Glu His Glu Val Phe Val Asn Ile Leu Lys
    50                  55                  60
```

```
Asp Asn Ser Val Glu Ile Glu Tyr Val Glu Asp Leu Val Ser Glu Val
 65                  70                  75                  80

Leu Ala Ser Ser Val Ala Leu Lys Asn Lys Phe Ile Ser Gln Phe Ile
                 85                  90                  95

Leu Glu Ala Glu Ile Lys Thr Asp Gly Val Ile Asn Ile Leu Lys Asp
            100                 105                 110

Tyr Phe Ser Asn Leu Thr Val Asp Asn Met Val Ser Lys Met Ile Ser
        115                 120                 125

Gly Val Ala Arg Glu Leu Lys Asp Cys Glu Phe Ser Leu Asp Asp
130                 135                 140

Trp Val Asn Gly Ser Ser Leu Phe Val Ile Asp Pro Met Pro Asn Val
145                 150                 155                 160

Leu Phe Thr Arg Asp Pro Phe Ala Ser Ile Gly Asn Gly Ile Thr Ile
                165                 170                 175

Asn Lys Met Tyr Thr Lys Val Arg Arg Arg Glu Thr Ile Phe Ala Glu
            180                 185                 190

Tyr Ile Phe Lys Tyr His Ser Ala Tyr Lys Glu Asn Val Pro Ile Trp
        195                 200                 205

Phe Asn Arg Trp Glu Glu Thr Ser Leu Glu Gly Gly Asp Glu Phe Val
    210                 215                 220

Leu Asn Lys Asp Leu Leu Val Ile Gly Ile Ser Glu Arg Thr Glu Ala
225                 230                 235                 240

Gly Ser Val Glu Lys Leu Ala Ala Ser Leu Phe Lys Asn Lys Ala Pro
                245                 250                 255

Phe Ser Thr Ile Leu Ala Phe Lys Ile Pro Lys Asn Arg Ala Tyr Met
            260                 265                 270

His Leu Asp Thr Val Phe Thr Gln Ile Asp Tyr Ser Val Phe Thr Ser
        275                 280                 285

Phe Thr Ser Asp Asp Met Tyr Phe Ser Ile Tyr Val Leu Thr Tyr Asn
    290                 295                 300

Ser Asn Ser Asn Lys Ile Asn Ile Lys Lys Glu Lys Ala Lys Leu Lys
305                 310                 315                 320

Asp Val Leu Ser Phe Tyr Leu Gly Arg Lys Ile Asp Ile Ile Lys Cys
                325                 330                 335

Ala Gly Gly Asp Leu Ile His Gly Ala Arg Glu Gln Trp Asn Asp Gly
            340                 345                 350

Ala Asn Val Leu Ala Ile Ala Pro Gly Glu Val Ile Ala Tyr Ser Arg
        355                 360                 365

Asn His Val Thr Asn Lys Leu Phe Glu Glu Asn Gly Ile Lys Val His
    370                 375                 380

Arg Ile Pro Ser Ser Glu Leu Ser Arg Gly Arg Gly Pro Arg Cys
385                 390                 395                 400

Met Ser Met Ser Leu Val Arg Glu Asp Ile
                405                 410

<210> SEQ ID NO 16
<211> LENGTH: 409
<212> TYPE: PRT
<213> ORGANISM: Borellia afzellii

<400> SEQUENCE: 16

Met Glu Glu Tyr Leu Asn Pro Ile Asn Ile Phe Ser Glu Ile Gly Arg
 1               5                  10                  15

Leu Lys Lys Val Leu Leu His Arg Pro Gly Glu Leu Glu Asn Leu
             20                  25                  30
```

```
Thr Pro Phe Ile Met Lys Asn Phe Leu Phe Asp Asp Ile Pro Tyr Leu
        35                  40                  45

Glu Val Ala Arg Gln Glu His Glu Val Phe Ala Ser Ile Leu Lys Asn
 50                  55                  60

Asn Leu Val Glu Ile Glu Tyr Ile Glu Asp Leu Ile Ser Glu Val Leu
 65                  70                  75                  80

Val Ser Ser Val Ala Leu Glu Asn Lys Phe Ile Ser Gln Phe Ile Leu
                 85                  90                  95

Glu Ala Glu Ile Lys Thr Asp Phe Thr Ile Asn Leu Leu Lys Asp Tyr
                100                 105                 110

Phe Ser Ser Leu Thr Ile Asp Asn Met Ile Ser Lys Met Ile Ser Gly
            115                 120                 125

Val Val Thr Glu Glu Leu Lys Asn Tyr Thr Ser Ser Leu Asp Asp Leu
        130                 135                 140

Val Asn Gly Ala Asn Leu Phe Ile Ile Asp Pro Met Pro Asn Val Leu
145                 150                 155                 160

Phe Thr Arg Asp Pro Phe Ala Ser Ile Gly Asn Gly Val Thr Ile Asn
                165                 170                 175

Lys Met Phe Thr Lys Val Arg Gln Arg Glu Thr Ile Phe Ala Glu Tyr
                180                 185                 190

Ile Phe Lys Tyr His Pro Val Tyr Lys Glu Asn Val Pro Ile Trp Leu
        195                 200                 205

Asn Arg Trp Glu Glu Ala Ser Leu Glu Gly Gly Asp Glu Leu Val Leu
    210                 215                 220

Asn Lys Gly Leu Leu Val Ile Gly Ile Ser Glu Arg Thr Glu Ala Lys
225                 230                 235                 240

Ser Val Glu Lys Leu Ala Ile Ser Leu Phe Lys Asn Lys Thr Ser Phe
                245                 250                 255

Asp Thr Ile Leu Ala Phe Gln Ile Pro Lys Asn Arg Ser Tyr Met His
                260                 265                 270

Leu Asp Thr Val Phe Thr Gln Ile Asp Tyr Ser Val Phe Thr Ser Phe
            275                 280                 285

Thr Ser Asp Asp Met Tyr Phe Ser Ile Tyr Val Leu Thr Tyr Asn Pro
        290                 295                 300

Ser Ser Ser Lys Ile His Ile Lys Lys Glu Lys Ala Arg Ile Lys Asp
305                 310                 315                 320

Val Leu Ser Phe Tyr Leu Gly Arg Lys Ile Asp Ile Lys Cys Ala
                325                 330                 335

Gly Gly Asp Leu Ile His Gly Ala Arg Glu Gln Trp Asn Asp Gly Ala
            340                 345                 350

Asn Val Leu Ala Ile Ala Pro Gly Glu Ile Ile Ala Tyr Ser Arg Asn
            355                 360                 365

His Val Thr Asn Lys Leu Phe Glu Glu Asn Gly Ile Lys Val His Arg
        370                 375                 380

Ile Pro Ser Ser Glu Leu Ser Arg Gly Arg Gly Pro Arg Cys Met
385                 390                 395                 400

Ser Met Pro Leu Ile Arg Glu Asp Ile
                405
```

<210> SEQ ID NO 17
<211> LENGTH: 580
<212> TYPE: PRT
<213> ORGANISM: Giardia intestinalis

<400> SEQUENCE: 17

```
Met Thr Asp Phe Ser Lys Asp Lys Glu Lys Leu Ala Gln Ala Thr Gln
1               5                   10                  15

Gly Gly Glu Asn Glu Arg Ala Glu Ile Val Val His Leu Pro Gln
            20                  25                  30

Gly Thr Ser Phe Leu Thr Ser Leu Asn Pro Glu Gly Asn Leu Leu Glu
            35                  40                  45

Glu Pro Ile Cys Pro Asp Glu Leu Arg Arg Asp His Glu Gly Phe Gln
        50                  55                  60

Ala Val Leu Lys Glu Lys Gly Cys Arg Val Tyr Met Pro Tyr Asp Val
65                  70                  75                  80

Leu Ser Glu Ala Ser Pro Ala Glu Arg Glu Val Leu Met Asp Gln Ala
                85                  90                  95

Met Ala Ser Leu Lys Tyr Glu Leu His Ala Thr Gly Ala Arg Ile Thr
            100                 105                 110

Pro Lys Met Lys Tyr Cys Val Ser Asp Glu Tyr Lys Arg Lys Val Leu
            115                 120                 125

Ser Ala Leu Ser Thr Arg Asn Leu Val Asp Val Ile Leu Ser Glu Pro
130                 135                 140

Val Ile His Leu Ala Pro Gly Val Arg Asn Thr Ala Leu Val Thr Asn
145                 150                 155                 160

Ser Val Glu Ile His Asp Ser Asn Asn Met Val Phe Met Arg Asp Gln
                165                 170                 175

Gln Ile Thr Thr Arg Arg Gly Ile Val Met Gly Gln Phe Gln Ala Pro
            180                 185                 190

Gln Arg Arg Arg Glu Gln Val Leu Ala Leu Ile Phe Trp Lys Arg Leu
            195                 200                 205

Gly Ala Arg Val Val Gly Asp Cys Arg Glu Gly Gly Pro His Cys Met
210                 215                 220

Leu Glu Gly Gly Asp Phe Val Pro Val Ser Pro Gly Leu Ala Met Met
225                 230                 235                 240

Gly Val Gly Leu Arg Ser Thr Tyr Val Gly Ala Gln Tyr Leu Met Ser
                245                 250                 255

Lys Asp Leu Leu Gly Thr Arg Arg Phe Ala Val Val Lys Asp Cys Phe
            260                 265                 270

Asp Gln His Gln Asp Arg Met His Leu Asp Cys Thr Phe Ser Val Leu
            275                 280                 285

His Asp Lys Leu Val Val Leu Asp Asp Tyr Ile Cys Ser Gly Met Gly
290                 295                 300

Leu Arg Tyr Val Asp Glu Trp Ile Asp Val Gly Ala Asp Ala Val Lys
305                 310                 315                 320

Lys Ala Lys Ser Ser Ala Val Thr Cys Gly Asn Tyr Val Leu Ala Lys
                325                 330                 335

Ala Asn Val Glu Phe Gln Gln Trp Leu Ser Glu Asn Gly Tyr Thr Ile
            340                 345                 350

Val Arg Ile Pro His Glu Tyr Gln Leu Ala Tyr Gly Cys Asn Asn Leu
            355                 360                 365

Asn Leu Gly Asn Asn Cys Val Leu Ser Val His Gln Pro Thr Val Asp
370                 375                 380

Phe Ile Lys Ala Asp Pro Ala Tyr Ile Ser Tyr Cys Lys Ser Asn Asn
385                 390                 395                 400

Leu Pro Asn Gly Leu Asp Leu Val Tyr Val Pro Phe Arg Gly Ile Thr
            405                 410                 415
```

-continued

```
Arg Met Tyr Gly Ser Leu His Cys Ala Ser Gln Val Val Tyr Arg Thr
            420                 425                 430
Pro Leu Ala Pro Ala Val Lys Ala Cys Glu Gln Glu Gly Asp Gly
        435                 440                 445
Ile Ala Ala Ile Tyr Glu Lys Asn Gly Glu Pro Val Asp Ala Ala Gly
    450                 455                 460
Lys Lys Phe Asp Cys Val Ile Tyr Ile Pro Ser Ser Val Asp Asp Leu
465                 470                 475                 480
Ile Asp Gly Leu Lys Ile Asn Leu Arg Asp Asp Ala Ala Pro Ser Arg
                485                 490                 495
Glu Ile Ile Ala Asp Ala Tyr Gly Leu Tyr Gln Lys Leu Val Ser Glu
                500                 505                 510
Gly Arg Val Pro Tyr Ile Thr Trp Arg Met Pro Ser Met Pro Val Val
            515                 520                 525
Ser Leu Lys Gly Ala Ala Lys Ala Gly Ser Leu Lys Ala Val Leu Asp
        530                 535                 540
Lys Ile Pro Gln Leu Thr Pro Phe Thr Pro Lys Ala Val Glu Gly Ala
545                 550                 555                 560
Pro Ala Ala Tyr Thr Arg Tyr Leu Gly Leu Glu Gln Ala Asp Ile Cys
                565                 570                 575
Val Asp Ile Lys
            580

<210> SEQ ID NO 18
<211> LENGTH: 413
<212> TYPE: PRT
<213> ORGANISM: Clostridium perfringens

<400> SEQUENCE: 18

Met Arg Asp Asp Arg Ala Leu Asn Val Thr Ser Glu Ile Gly Arg Leu
1               5                   10                  15
Lys Thr Val Leu Leu His Arg Pro Gly Glu Ile Glu Asn Leu Thr
            20                  25                  30
Pro Asp Leu Leu Asp Arg Leu Leu Phe Asp Asp Ile Pro Tyr Leu Lys
        35                  40                  45
Val Ala Arg Glu Glu His Asp Ala Phe Ala Gln Thr Leu Arg Glu Ala
    50                  55                  60
Gly Val Glu Val Leu Tyr Leu Glu Val Leu Ala Ala Glu Ala Ile Glu
65                  70                  75                  80
Thr Ser Asp Glu Val Lys Gln Gln Phe Ile Ser Glu Phe Ile Asp Glu
                85                  90                  95
Ala Gly Val Glu Ser Glu Arg Leu Lys Glu Ala Leu Ile Glu Tyr Phe
                100                 105                 110
Asn Ser Phe Ser Asp Asn Lys Ala Met Val Asp Lys Met Met Ala Gly
            115                 120                 125
Val Arg Lys Glu Glu Leu Lys Asp Tyr His Arg Glu Ser Leu Tyr Asp
        130                 135                 140
Gln Val Asn Asn Val Tyr Pro Phe Val Cys Asp Pro Met Pro Asn Leu
145                 150                 155                 160
Tyr Phe Thr Arg Glu Pro Phe Ala Thr Ile Gly His Gly Ile Thr Leu
                165                 170                 175
Asn His Met Arg Thr Asp Thr Arg Asn Arg Glu Thr Ile Phe Ala Lys
                180                 185                 190
Tyr Ile Phe Arg His His Pro Arg Phe Glu Gly Lys Asp Ile Pro Phe
            195                 200                 205
```

```
Trp Phe Asn Arg Asn Asp Lys Thr Ser Leu Glu Gly Gly Asp Glu Leu
    210                 215                 220

Ile Leu Ser Lys Glu Ile Leu Ala Val Gly Ile Ser Gln Arg Thr Asp
225                 230                 235                 240

Ser Ala Ser Val Glu Lys Leu Ala Lys Lys Leu Leu Tyr Tyr Pro Asp
                245                 250                 255

Thr Ser Phe Lys Thr Val Leu Ala Phe Lys Ile Pro Val Ser Arg Ala
            260                 265                 270

Phe Met His Leu Asp Thr Val Phe Thr Gln Val Asp Tyr Asp Lys Phe
        275                 280                 285

Thr Val His Pro Gly Ile Val Gly Pro Leu Glu Val Tyr Ala Leu Thr
    290                 295                 300

Lys Asp Pro Glu Asn Asp Gly Gln Leu Leu Val Thr Glu Glu Val Asp
305                 310                 315                 320

Thr Leu Glu Asn Ile Leu Lys Lys Tyr Leu Asp Arg Asp Ile Lys Leu
                325                 330                 335

Ile Lys Cys Gly Gly Asp Glu Ile Ile Ala Ala Arg Glu Gln Trp
            340                 345                 350

Asn Asp Gly Ser Asn Thr Leu Ala Ile Ala Pro Gly Glu Val Val Val
        355                 360                 365

Tyr Ser Arg Asn Tyr Val Thr Asn Glu Ile Leu Glu Lys Gly Ile
370                 375                 380

Lys Leu His Val Ile Pro Ser Ser Glu Leu Ser Arg Gly Arg Gly Gly
385                 390                 395                 400

Pro Arg Cys Met Ser Met Pro Leu Ile Arg Glu Asp Leu
                405                 410

<210> SEQ ID NO 19
<211> LENGTH: 413
<212> TYPE: PRT
<213> ORGANISM: Bacillus licheniformis

<400> SEQUENCE: 19

Met Ile Met Thr Thr Pro Ile His Val Tyr Ser Glu Ile Gly Pro Leu
1               5                   10                  15

Lys Thr Val Met Leu Lys Arg Pro Gly Arg Glu Leu Glu Asn Leu Thr
                20                  25                  30

Pro Glu Tyr Leu Glu Arg Leu Leu Phe Asp Asp Ile Pro Phe Leu Pro
            35                  40                  45

Ala Val Gln Lys Glu His Asp Gln Phe Ala Glu Thr Leu Lys Gln Gln
        50                  55                  60

Gly Ala Glu Val Leu Tyr Leu Glu Lys Leu Thr Ala Glu Ala Leu Asp
65                  70                  75                  80

Asp Ala Leu Val Arg Glu Gln Phe Ile Asp Glu Leu Leu Thr Glu Ser
                85                  90                  95

Lys Ala Asp Ile Asn Gly Ala Tyr Asp Arg Leu Lys Glu Phe Leu Leu
                100                 105                 110

Thr Phe Asp Ala Asp Ser Met Val Glu Gln Val Met Ser Gly Ile Arg
            115                 120                 125

Lys Asn Glu Leu Glu Arg Glu Lys Lys Ser His Leu His Glu Leu Met
        130                 135                 140

Glu Asp His Tyr Pro Phe Tyr Leu Asp Pro Met Pro Asn Leu Tyr Phe
145                 150                 155                 160

Thr Arg Asp Pro Ala Ala Ala Ile Gly Ser Gly Leu Thr Ile Asn Lys
                165                 170                 175
```

Met Lys Glu Pro Ala Arg Arg Arg Glu Ser Leu Phe Met Arg Tyr Ile
            180                 185                 190

Ile Asn His His Pro Arg Phe Lys Gly His Glu Ile Pro Val Trp Leu
            195                 200                 205

Asp Arg Asp Phe Lys Phe Asn Ile Glu Gly Gly Asp Glu Leu Val Leu
            210                 215                 220

Asn Glu Glu Thr Val Ala Ile Gly Val Ser Glu Arg Thr Thr Ala Gln
225                 230                 235                 240

Ala Ile Glu Arg Leu Val Arg Asn Leu Phe Gln Arg Gln Ser Arg Ile
                245                 250                 255

Arg Arg Val Leu Ala Val Glu Ile Pro Lys Ser Arg Ala Phe Met His
            260                 265                 270

Leu Asp Thr Val Phe Thr Met Val Asp Arg Asp Gln Phe Thr Ile His
            275                 280                 285

Pro Ala Ile Gln Gly Pro Glu Gly Asp Met Arg Ile Phe Val Leu Glu
            290                 295                 300

Arg Gly Lys Thr Ala Asp Glu Ile His Thr Thr Glu His Asn Leu
305                 310                 315                 320

Pro Glu Val Leu Lys Arg Thr Leu Gly Leu Ser Asp Val Asn Leu Ile
                325                 330                 335

Phe Cys Gly Gly Asp Glu Ile Ala Ser Ala Arg Glu Gln Trp Asn
            340                 345                 350

Asp Gly Ser Asn Thr Leu Ala Ile Ala Pro Gly Val Val Thr Tyr
            355                 360                 365

Asp Arg Asn Tyr Ile Ser Asn Glu Cys Leu Arg Glu Gln Gly Ile Lys
            370                 375                 380

Val Ile Glu Ile Pro Ser Gly Glu Leu Ser Arg Gly Arg Gly Pro
385                 390                 395                 400

Arg Cys Met Ser Met Pro Leu Tyr Arg Glu Asp Val Lys
            405                 410

<210> SEQ ID NO 20
<211> LENGTH: 408
<212> TYPE: PRT
<213> ORGANISM: Enterococcus faecalis

<400> SEQUENCE: 20

Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
            20                  25                  30

Tyr Leu Glu Arg Leu Leu Phe Asp Asp Ile Pro Phe Leu Glu Lys Ala
            35                  40                  45

Gln Ala Glu His Asp Ala Phe Ala Glu Leu Leu Arg Ser Lys Asp Ile
            50                  55                  60

Glu Val Val Tyr Leu Glu Asp Leu Ala Ala Glu Ala Leu Ile Asn Glu
65                  70                  75                  80

Glu Val Arg Arg Gln Phe Ile Asp Gln Phe Leu Glu Glu Ala Asn Ile
                85                  90                  95

Arg Ser Glu Ser Ala Lys Glu Lys Val Arg Glu Leu Met Leu Glu Ile
            100                 105                 110

Asp Asp Asn Glu Glu Leu Ile Gln Lys Ala Ile Ala Gly Ile Gln Lys
            115                 120                 125

Gln Glu Leu Pro Lys Tyr Glu Gln Glu Phe Leu Thr Asp Met Val Glu
130                 135                 140

-continued

```
Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
                165                 170                 175

Tyr Ser Val Thr Arg Gln Arg Glu Thr Ile Phe Gly Gln Tyr Ile Phe
            180                 185                 190

Asp Tyr His Pro Arg Phe Ala Gly Lys Glu Val Pro Arg Val Tyr Asp
        195                 200                 205

Arg Ser Glu Ser Thr Arg Ile Glu Gly Gly Asp Glu Leu Ile Leu Ser
    210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Gly Glu His Arg Lys Phe Met His Leu
            260                 265                 270

Asp Thr Val Phe Thr Met Ile Asp Tyr Asp Lys Phe Thr Ile His Pro
        275                 280                 285

Glu Ile Glu Gly Gly Leu Val Val Tyr Ser Ile Thr Glu Lys Ala Asp
    290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
                325                 330                 335

Gly Asn Leu Thr Ala Ala Ala Arg Glu Gln Trp Asn Asp Gly Ser Asn
            340                 345                 350

Thr Leu Ala Ile Ala Pro Gly Glu Val Val Tyr Asp Arg Asn Thr
        355                 360                 365

Ile Thr Asn Lys Ala Leu Glu Glu Ala Gly Val Lys Leu Asn Tyr Ile
    370                 375                 380

Pro Gly Ser Glu Leu Val Arg Gly Arg Gly Pro Arg Cys Met Ser
385                 390                 395                 400

Met Pro Leu Tyr Arg Glu Asp Leu
                405
```

<210> SEQ ID NO 21
<211> LENGTH: 409
<212> TYPE: PRT
<213> ORGANISM: Lactobacillus sake

<400> SEQUENCE: 21

```
Met Thr Ser Pro Ile His Val Asn Ser Glu Ile Gly Lys Leu Lys Thr
1               5                   10                  15

Val Leu Leu Lys Arg Pro Gly Lys Glu Val Glu Asn Ile Thr Pro Asp
                20                  25                  30

Ile Met Tyr Arg Leu Leu Phe Asp Ile Pro Tyr Leu Pro Thr Ile
            35                  40                  45

Gln Lys Glu His Asp Gln Phe Ala Gln Thr Leu Arg Asp Asn Gly Val
        50                  55                  60

Glu Val Leu Tyr Leu Glu Asn Leu Ala Ala Glu Ala Ile Asp Ala Gly
65                  70                  75                  80

Asp Val Lys Glu Ala Phe Leu Asp Lys Met Leu Asn Glu Ser His Ile
                85                  90                  95

Lys Ser Pro Gln Val Gln Ala Ala Leu Lys Asp Tyr Leu Ile Ser Met
            100                 105                 110
```

-continued

```
Ala Thr Leu Asp Met Val Glu Lys Ile Met Ala Gly Val Arg Thr Asn
        115                 120                 125

Glu Ile Asp Ile Lys Ser Lys Ala Leu Ile Asp Val Ser Ala Asp Asp
    130                 135                 140

Asp Tyr Pro Phe Tyr Met Asp Pro Met Pro Asn Leu Tyr Phe Thr Arg
145                     150                 155                 160

Asp Pro Ala Ala Ser Met Gly Asp Gly Leu Thr Ile Asn Lys Met Thr
                165                 170                 175

Phe Glu Ala Arg Gln Arg Glu Ser Met Phe Met Glu Val Ile Met Gln
            180                 185                 190

His His Pro Arg Phe Ala Asn Gln Gly Ala Gln Val Trp Arg Asp Arg
        195                 200                 205

Asp His Ile Asp Arg Met Glu Gly Gly Asp Glu Leu Ile Leu Ser Asp
    210                 215                 220

Lys Val Leu Ala Ile Gly Ile Ser Gln Arg Thr Ser Ala Gln Ser Ile
225                 230                 235                 240

Glu Glu Leu Ala Lys Val Leu Phe Ala Asn His Ser Gly Phe Glu Lys
                245                 250                 255

Ile Leu Ala Ile Lys Ile Pro His Lys His Ala Met Met His Leu Asp
            260                 265                 270

Thr Val Phe Thr Met Ile Asp Tyr Asp Lys Phe Thr Ile His Pro Gly
        275                 280                 285

Ile Gln Gly Ala Gly Gly Met Val Asp Thr Tyr Ile Leu Glu Pro Gly
    290                 295                 300

Asn Asn Asp Glu Ile Lys Ile Thr His Gln Thr Asp Leu Glu Lys Val
305                 310                 315                 320

Leu Arg Asp Ala Leu Glu Val Pro Glu Leu Thr Leu Ile Pro Cys Gly
                325                 330                 335

Gly Gly Asp Ala Val Val Ala Pro Arg Glu Gln Trp Asn Asp Gly Ser
            340                 345                 350

Asn Thr Leu Ala Ile Ala Pro Gly Val Val Val Thr Tyr Asp Arg Asn
        355                 360                 365

Tyr Val Ser Asn Glu Asn Leu Arg Gln Tyr Gly Ile Lys Val Ile Glu
    370                 375                 380

Val Pro Ser Ser Glu Leu Ser Arg Gly Arg Gly Gly Pro Arg Cys Met
385                 390                 395                 400

Ser Met Pro Leu Val Arg Arg Lys Thr
                405
```